US011185534B2

(12) United States Patent
Slusher et al.

(10) Patent No.: US 11,185,534 B2
(45) Date of Patent: Nov. 30, 2021

(54) PRODRUGS OF GLUTAMINE ANALOGS

(71) Applicants: The Johns Hopkins University, Baltimore, MD (US); Ústav organické chemie a biochemie AV ČR, v.v.i., Prague (CZ)

(72) Inventors: Barbara Slusher, Kingsville, MD (US); Pavel Majer, Sykesville, MD (US); Lukas Tenora, Prague (CZ); Katerina Novotna, Prague (CZ); Peter Michael Hudlicky, Prague (CZ)

(73) Assignees: The Johns Hopkins University, Baltimore, MD (US); Ústav organické Chemie a biochemie AV Č R, v.v.i., Prague (CZ)

( * ) Notice: Subject to any disclaimer, the term of this patent is extended or adjusted under 35 U.S.C. 154(b) by 0 days.

(21) Appl. No.: 16/482,957

(22) PCT Filed: Feb. 1, 2018

(86) PCT No.: PCT/US2018/016428
§ 371 (c)(1),
(2) Date: Aug. 1, 2019

(87) PCT Pub. No.: WO2018/144718
PCT Pub. Date: Aug. 9, 2018

(65) Prior Publication Data
US 2020/0230111 A1     Jul. 23, 2020

Related U.S. Application Data

(60) Provisional application No. 62/453,243, filed on Feb. 1, 2017.

(51) Int. Cl.
*A61K 31/422*     (2006.01)
*C07D 261/04*     (2006.01)
*C07D 413/12*     (2006.01)

(52) U.S. Cl.
CPC ................. *A61K 31/422* (2013.01)

(58) Field of Classification Search
CPC ... A61K 31/422; C07D 261/04; C07D 413/12
See application file for complete search history.

(56) References Cited

U.S. PATENT DOCUMENTS

| | | | |
|---|---|---|---|
| 4,256,898 | A | 3/1981 | Kelly et al. |
| 4,970,297 | A | 11/1990 | Castelhano et al. |
| 5,770,576 | A | 6/1998 | Morozov et al. |
| 6,126,939 | A | 10/2000 | Eisenbach-Schwartz et al. |
| 9,944,592 | B2 | 4/2018 | Gallop et al. |
| 10,336,778 | B2 | 7/2019 | Slusher et al. |
| 2004/0029801 | A1 | 2/2004 | Zhong et al. |
| 2008/0107623 | A1 | 5/2008 | D'Andrea et al. |
| 2009/0062223 | A1 | 3/2009 | Keicher et al. |
| 2013/0017266 | A1 | 1/2013 | Ogino et al. |

FOREIGN PATENT DOCUMENTS

| | | | | |
|---|---|---|---|---|
| WO | WO-8101145 A1 | * | 4/1981 | ........... C07K 5/0804 |
| WO | WO-2005068455 A1 | | 7/2005 | |
| WO | WO-2005097108 A1 | | 10/2005 | |
| WO | WO-2018144718 A1 | | 8/2018 | |
| WO | WO-2019071110 A1 | | 4/2019 | |

OTHER PUBLICATIONS

CAS Registry Entry for Registry No. 42228-92-2, which entered STN on Nov. 16, 1984 (Year: 1984).*
Kelly et al. J. Am. Chem. Soc. 1979, 101, 1054-1056 (Year: 1979).*
Tamborini et al. ChemMedChem 2012, 7, 1623-1634 (Year: 2012).*
Ahluwalia.,G.S., et.al., "Metabolism and Action of Amino Acid Analog Anti-cancer Agents.," Pharmacology & Therapeutics 46(2):243-271, Pergamon Press, England (1990).
Alt,J., et.al., "Bioanalysis of 6-diazo-5-oxo-l-norleucine in Plasma and Brain by Ultra-performance Liquid Chromatography Mass Spectrometry," Analytical Biochemistry 474:28-34, Elsevier, United States (Apr. 2015).
Antczak, C., et al., "A New Acivicin Prodrug Designed For Tumor-Targeted Delivery," Bioorganic & Medicinal Chemistry, 9(11):2843-2848, Elsevier Science, England (Nov. 2001).
Barclay, R.K., et.al., "Effects of 6-diazo-5-oxol-norleucine and OtherTumor Inhibitors on the Biosynthesis of Nicotinamide Adenine Dinucleotide in Mice.," Cancer research 26(2):282-286, American Association for Cancer Research, United States (Feb. 1966).
Berge, S.M., et al., "Pharmaceutical Salts," Journal of Pharmaceutical Sciences 66(1): 1-19, Wiley, United States (Jan. 1977).
Carr, E.L., et.al., "Glutamine Uptake and Metabolism are Coordinately Regulated by Erk/mapk During T Lymphocyte Activation.," Journal of Immunology (Baltimore, Md. : 1950) 185(2):1037-1044, American Association of Immunologists, United States (Jul. 2010).
Cervantes-Madrid, D., et al., "Reviving Lonidamine and 6-Diazo-5-oxo-L-norleucine to be used in Combination for Metabolic Cancer Therapy," BioMed Research International 2015:690492, Hindawi Pub. Co, United States (2015).
Chung, S.H and Johnson, M.S., "Studies on Sound-induced Epilepsy in Mice," Proceedings of the Royal Society of London. Series B, Biological sciences, 221(1223):145-168, Printed for the Royal Society and sold by Harrison & Sons, England (Apr. 1984).
Cinatl, J., et al., "Antiviral Effects of 6-diazo-5-oxo-L-norleucin on Replication of Herpes Simplex Virus Type 1," Antiviral Research 33(3):165-175, Elsevier, Netherlands (Feb. 1997).
Coffey, G.L., et al., "6-diazo-5-oxo-L-norleucine, a New Tumor-inhibitory Substance. I. Biologic Studies," Antibiotics & Chemotherapy 6(8):487-497, Washington Institute of Medicine, United States (Aug. 1956).
Coggin, JR.J.H.and Martin, W. R., "6-Diazo-5-Oxo-l-Norleucine Inhibition of *Escherichia coli*," Journal of Bacteriology 89(5):1348-1353, American Society For Microbiology, United States (May 1965).

(Continued)

*Primary Examiner* — Matthew P Coughlin
(74) *Attorney, Agent, or Firm* — Sterne, Kessler, Goldstein & Fox P.L.L.C.

(57) ABSTRACT

Prodrugs of glutamine analogs, such as prodrugs of acivicin, are disclosed.

4 Claims, No Drawings

(56) References Cited

OTHER PUBLICATIONS

Colombo, S.L., et al., "Anaphase-promoting Complex/cyclosome-cdh1 Coordinates Glycolysis and Glutaminolysis With Transition to S Phase in Human T Lymphocytes," Proceedings of the National Academy of Sciences of the United States of America, 107(44):18868-18873, National Academy of Sciences, United States (Nov. 2010).
Deberardinis, R.J. and Cheng, T., "Q's Next: the Diverse Functions of Glutamine in Metabolism, Cell Biology and Cancer," Oncogene 29(3):313-324, Nature Publishing Group, England (Jan. 2010).
Dion, H.W., et al., "6-Diazo-5-oxo-L-norleucine, A New Tumor-inhibitory Substance. II. Isolation and Characterization," Journal of the American Chemical Society 78(13):3075-3077, (Jul. 1956).
Dranoff, G., et al., "Combination Chemotherapy in Vitro Exploiting Glutamine Metabolism of Human Glioma and Medulloblastoma," Cancer Research 45(9):4082-4086, American Association for Cancer Research, United States (Sep. 1985).
Dranoff, G., et al., "Influence of Glutamine on the Growth of Human Glioma and Medulloblastoma in Culture," Cancer Research 45(9):4077-4081, American Association for Cancer Research, United States (Sep. 1985).
Eagan, R.T., et al., "Phase II Study on DON in Patients with Previously Treated Advanced Lung Cancer," Cancer Treatment Reports 66(8):1665-1666, National Cancer Institute, United States (Aug. 1982).
Earhart, R.H., et al., "Phase I Trial of 6-diazo-5-oxo-L-norleucine (DON) Administered by 5-day Courses," Cancer Treatment Reports 66(5):1215-1217, National Cancer Institute, United States (May 1982).
Earhart, R.H., et al., "Phase II Trial of 6-diazo-5-oxo-L-norleucine Versus Aclacinomycin-a in Advanced Sarcomas and Mesotheliomas," Investigational New Drugs 8(1):113-119, Springer, United States (Feb. 1990).
Erickson, J.W. and Cerione R.A., "Glutaminase: A Hot Spot for Regulation of Cancer Cell Metabolism?," Oncotarget 1(8):734-740, Impact Journals, United States (Dec. 2010).
Eshleman, J.S., et al., "Inhibition of the Mammalian Target of Rapamycin Sensitizes U87 Xenografts to Fractionated Radiation Therapy," Cancer Research 62(24):7291-7297, American Association for Cancer Research, United States (Dec. 2002).
Fogal, V., et al., "Mitochondrial p32 is Upregulated in Myc Expressing Brain Cancers and Mediates Glutamine Addiction," Oncotarget 6(2):1157-1170, Impact Journals, United States (Jan. 2015).
Grayzel, A.I., et al., "Suppression of Uric Acid Synthesis in the Gouty Human by the Use of 6-diazo-5-oxo-L-norleucine.," The Journal of Clinical Investigation 39:447-454, American Society for Clinical Investigation, United States (Mar. 1960).
Gross, M.I., et al., "Antitumor Activity of the Glutaminase Inhibitor CB-839 in Triple-Negative Breast Cancer," Molecular Cancer Therapeutics 13(4):890-901, American Association for Cancer Research, United States (Apr. 2014).
Harding, J.J., et al., "Safety and Tolerability of Increasing Doses of CB-839, a First-in-class, Orally Administered Small Molecule Inhibitor of Glutaminase, in Solid Tumors," Journal of Clinical Oncology 33(15_suppl.2512), (May 2015).
Hensley, C.T., et al., "Glutamine and Cancer: Cell Biology, Physiology, and Clinical Opportunities," The Journal of Clinical Investigation 123(9):3678-3684, American Society for Clinical Investigation, United States (Sep. 2013).
Hofer, A., et al., "Trypanosoma Brucei CTP Synthetase: a Target for the Treatment of African Sleeping Sickness," Proceedings of the National Academy of Sciences of the United States of America 98(11):6412-6416, National Academy of Sciences, United States (May 2001).
Hu, X., et al., "Genetic Alterations and Oncogenic Pathways Associated with Breast Cancer Subtypes," Molecular Cancer Research 7(4):511-522, American Association for Cancer Research, United States (Apr. 2009).

Huang, R.C., et al., "Inhibition of Replication of Human Respiratory Syncytial Virus by 6-Diazo-5-Oxo-L-Norleucine," Antiviral Research, 25(3-4):269-279, Elsevier, Netherlands (Dec. 1994).
Huber, K.R., "Uptake of Glutamine Antimetabolites 6-Diazo-5-Oxo-L-Norleucine (Don) and Acivicin in Sensitive and Resistant Tumor Cell Lines," International Journal of Cancer, 41(5):752-755, Wiley-Liss, United States (May 1988).
Konopleva, M.Y., et al., "Phase 1 Study: Safety and Tolerability of Increasing Doses of Cb-839, an Orally-administered Small Molecule Inhibitor of Glutaminase, in Acute Leukemia," Haematologica, 99749; E947 (Jun. 2015).
Kulcsar, K.A., et al., "Interleukin 10 Modulation of Pathogenic Th17 Cells During Fatal Alphavirus Encephalomyelitis," Proceedings of the National Academy of Sciences of the United States of America, 111(45):16053-16058, National Academy of Sciences, United States (Nov. 2014).
Le, A., et al., "Glucose-independent Glutamine Metabolism via TCA Cycling for Proliferation and Survival in B Cells," Cell Metabolism 15(1):110-121, Cell Press, United States (Jan. 2012).
Lee, Y.Z., et al., "Discovery of Selective Inhibitors of Glutaminase-2, which Inhibit mTORC1, Activate Autophagy and Inhibit Proliferation in Cancer Cells," Oncotarget 5(15):6087-6101, Impact Journals, United States (Aug. 2014).
Lynch, G., et al., "Phase II Evaluation of DON (6-diazo-5-oxo-L-norleucine) in Patients with Advanced Colorectal Carcinoma," American Journal of Clinical Oncology 5(5):541-543, Lippincott Williams & Wilkins, United States (Oct. 1982).
Maciolek, J.A., at al., "Metabolism of Activated T Lymphocytes," Current Opinion in Immunology, 27:60-74, Elsevier, England (Apr. 2014).
Magill, G.B. and Myers, W.P., "Alterations in Calcium Metabolism in Cancer Patients Treated with 6-diazo-5-oxo-L-norleucine," Proceedings of the Society for Experimental Biology and Medicine 93(2):314-318, Blackwell Science, United States (Nov. 1956).
Magill, G.B., et al., "Pharmacological and Initial Therapeutic Observations on 6-diazo-5-oxo-1-norleucine (DON) in Human Neoplastic Disease," Cancer 10(6):1138-1150, Wiley, United States (Nov.-Dec. 1957).
McDermott, L.A., et al., "Design and Evaluation of Novel Glutaminase Inhibitors," Bioorganic & Medicinal Chemistry 24(8):1819-1839, Elsevier Science, England (Apr. 2016).
Medina, M.A., et al., "Relevance of Glutamine Metabolism to Tumor Cell Growth," Molecular and Cellular Biochemistry 113(1):1-15, Springer, Netherlands (Jul. 1992).
Nongonierma, A.B and Fitzgerald, R.J., "Inhibition of Dipeptidyl Peptidase IV (DPP-IV) by Tryptophan Containing Dipeptides," Food & Function, 4(12):1843-1849, Royal Society of Chemistry, England (Dec. 2013).
Ostrom, Q.T., et al., "CBTRUS Statistical Report: Primary Brain and Central Nervous System Tumors Diagnosed in the United States in 2008-2012," Neuro-oncology 17(Suppl 4):iv1-iv62, Oxford University Press, England (Oct. 2015).
Potter, M.C., et al., "Neurological Sequelae Induced by Alphavirus Infection of the CNS are Attenuated by Treatment with the Glutamine Antagonist 6-diazo-5-oxo-l-norleucine," Journal of Neurovirology 21(2):159-173, Stockton Press, United States (Apr. 2015).
Rahman, A., et al., "Phase I Study and Clinical Pharmacology of 6-diazo-5-oxo-L-norleucine (DON)," Investigational New Drugs 3(4):369-374, Springer, United States (1985).
Rautio, J., et al., "Prodrugs: Design and Clinical Applications," Nature Reviews. Drug Discovery 7(3):255-270, Nature Publishing Group, England (Mar. 2008).
Ru, P., et al., "Tumor Metabolism of Malignant Gliomas," Cancers 5(4):1469-1484, MDPI, Switzerland (Dec. 2013).
Schulze, A. and Harris, A.L., "How Cancer Metabolism is Tuned for Proliferation and Vulnerable to Disruption," Nature 491(7424):364-373, Nature Publishing Group, England (Nov. 2012).
Shijie, J., et al., "Blockade of Glutamate Release from Microglia Attenuates Experimental Autoimmune Encephalomyelitis in Mice," Tohoku Journal of Experimental Medicine, 217(2):87-92, Tohoku University Medical Library, Japan (Feb. 2009).
Shukla, K., et al., "Design, Synthesis, and Pharmacological Evaluation of Bis-2-(5-phenylacetamido-1,2,4-thiadiazol-2-yl)ethyl Sul-

(56) References Cited

OTHER PUBLICATIONS fide 3 (BPTES) Analogs as Glutaminase Inhibitors," Journal of Medicinal Chemistry 55(23):10551-10563, American Chemical Society, United States (Dec. 2012).

Sklaroff, R.B., et al., "Phase I Study of 6-diazo-5-oxo-L-norleucine (DON)," Cancer Treatment Reports 64(12):1247-1251, National Cancer Institute, United States (1980).

Stupp, R., et al., "Effects of Radiotherapy with Concomitant and Adjuvant Temozolomide Versus Radiotherapy Alone on Survival in Glioblastoma in a Randomised Phase III Study: 5-year Analysis of the EORTC-NCIC Trial," The Lancet. Oncology 10(5):459-466, Lancet Pub. Group, England (May 2009).

Stupp, R., et al., "Radiotherapy Plus Concomitant and Adjuvant Temozolomide for Glioblastoma," The New England Journal of Medicine 352(10):987-996, Massachusetts Medical Society, United States (Mar. 2005).

Sullivan, M.P., et al., "A Comparison of the Effectiveness of Standard Dose 6-mercaptopurine, Combination 6-mercaptopurine and DON, and High-loading 6-mercaptopurine Therapies in Treatment of the Acute Leukemias of Childhood: Results of a Coperative Study," Cancer Chemotherapy Reports 18:83-95, National Cancer Institute, United States (May 1962).

Sullivan, M.P., et al., "Pharmacokinetic and Phase I Study of Intravenous DON (6-diazo-5-oxo-L-norleucine) in Children," Cancer Chemotherapy Reports 21(1):78-84, Springer Verlag, Germany (1988).

Tanaka, K., et al., "Compensatory Glutamine Metabolism Promotes Glioblastoma Resistance to mTOR Inhibitor Treatment," The Journal of Clinical Investigation 125(4):1591-1602, American Society for Clinical Investigation, United States (Apr. 2015).

Thangavelu, K., et al., "Structural Basis for the Active Site Inhibition Mechanism of Human Kidney-type Glutaminase (KGA)," Scientific Reports 4:3827, Nature Publishing Group, England (Jan. 2014).

Upadhyay, R.K., "Drug Delivery Systems, CNS Protection, and the Blood Brain Barrier," BioMed Research International 2014:869269, Hindawi Pub. Co, United States (2014).

Weller, M., et al., "EANO Guideline for the Diagnosis and Treatment of Anaplastic Gliomas and Glioblastoma.," The Lancet. Oncology 15(9):e395-403, Lancet Pub. Group, England (Aug. 2014).

Willis, R.C. and Seegmiller, J.E., "The Inhibition by 6-diazo-5-oxo-L-norleucine of Glutamine Catabolism of the Cultured Human Lymphoblast," Journal of Cellular Physiology 93(3):375-382, Wiley-Liss, United States (Dec. 1977).

Windmueller, H.G. and Spaeth, A.E., "Uptake and Metabolism of Plasma Glutamine by the Small Intestine," The Journal of Biological Chemistry 249(16):5070-5079, American Society for Biochemistry and Molecular Biology, United States (Aug. 1974).

Wise, D.R. and Thompson, C.B., "Glutamine Addiction: a New Therapeutic Target in Cancer," Trends in Biochemical Sciences 35(8):427-433, Elsevier Trends Journals, England (Aug. 2010).

Yoshioka, K., et al., "Glutamine Antagonist with Diet Deficient in Glutamine and Aspartate Reduce Tumor Growth," Tokushima Journal of Experimental Medicine, 39(1-2):69-76, Tokushima University. School of Medicine, Japan (Jun. 1992).

Chakravarty, P.K., et al., "Plasmin-activated prodrugs for cancer chemotherapy. 1. Synthesis and biological activity of peptidylacivicin and peptidylphenylenediamine mustard," *J Med Chem* 26(5):633-638, American Chemical Society, United States (1983).

Extended European Search Report for European Application No. EP 18 74 7375, Munich, Germany, dated Aug. 6, 2020, 9 pages.

\* cited by examiner

PRODRUGS OF GLUTAMINE ANALOGS

BACKGROUND

The prodrug approach is a well-established strategy to improve physicochemical, biopharmaceutic and pharmacokinetic properties of potential drug molecules. Approximately 5-7% of drugs approved worldwide are prodrugs with annual sales in 2013 of $11.2 billion. Most prodrugs are simple chemical derivatives of the original molecule. Ester prodrugs, the most common prodrugs, constitute 49% of all marketed prodrugs. Reasons for the popularity of ester prodrugs include their generally straight forward synthesis, their improved lipophilicity and membrane permeability, and the ubiquitousness of estereases. An example of an approach to make an ester prodrug is capping the acidic moiety (ies) with lipophilic alkyl or alkyloxymethyl esters (i.e., pivaloyloxymethyl (POM) or propyloxy-carbonyloxymethyl (POC); e.g., Enalapril, Adefovir). Another approach is to cap the acidic moiety(ies) with amino acids to make amides that are recognizable by amidases/peptidases in plasma for hydrolysis or to make them substrates for transporters, such as Peptide transporter 1 (PEPT1) (e.g., Pomaglumetad methionil, Valacyclovir).

Glutamine antagonists, such as acivicin, have been shown to exhibit broad anti-viral (Antiviral Res. 1997; 33(3):165-75; Antiviral Res. 1994; 25(3-4):269-79), anti-infective (J. Bacteriol. 1965; 89:1348-53), anti-cancer (see, e.g., Yoshioka et al., 1992; *Tokushima J. Exp. Med.* 39(1-2):69-76), anti-inflammatory, and immunosuppressive activities (Kulcsar et al., 2014; 111:16053-58; Maciolek et al., 2014; *Curr Opin Immunol.* 27:60-74; Carr et al., 2010; *J Immunol.* 185:1037-1044; Colombo et al., 2010; *Proc Natl Acad Sci USA.* 107:18868-73), as well as inhibition of convulsions (Proc R Soc Lond B Biol Sci. 1984 Apr. 24; 221(1223): 145-68), multiple sclerosis (Tohoku, J. Exp. Med. 2009; 217(2):87-92), epilepsy, and viral encephalitis (J. Neurovirol. 2015 April; 21(2):159-73), in many published preclinical and several clinical studies. The occurrence of severe toxicity, however, (e.g., dose limiting GI toxicities, such as oral mucosistis, gastric bleeding, nausea and vomiting, abdominal pain, leukopenia, thrombocytopenia, and the like) when administering such glutamine antagonists at therapeutic dose levels has hampered their clinical development. Prior attempts to mitigate the severe toxicity associated with glutamine antagonists have been unsuccessful.

SUMMARY

The presently disclosed subject matter provides prodrugs of acivicin, and pharmaceutically acceptable salts and esters thereof. In some aspects, the presently disclosed subject matter provides a prodrug of acivicin, or a pharmaceutically acceptable salt or ester thereof, the prodrug having a structure of formula (I):

A prodrug of acivicin, or a pharmaceutically acceptable salt or ester thereof, the prodrug having a structure of formula (I):

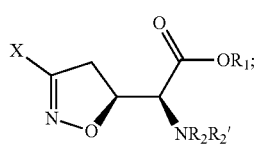

(I)

wherein:
$R_1$ is selected from the group consisting of H and a first prodrug-forming moiety, or a residue thereof, capable of forming a salt or an ester; and
$R_2$ is H or a second prodrug-forming moiety, or a residue thereof, capable of forming an amide linkage, a carbamate linkage, a phosphoramidate linkage or a phosphorodiamidate linkage with the nitrogen adjacent to $R_2$;
$R_2'$ is selected from the group consisting of H, $C_1$-$C_6$ alkyl, substituted $C_1$-$C_6$ alkyl, substituted or unsubstituted succinyl, and substituted or unsubstituted glutamyl, or
$R_2$ and $R_2'$ together form a ring structure comprising —C(=O)-G-C(=O)—, wherein G is selected from the group consisting of $C_1$-$C_8$ alkylene, $C_1$-$C_8$ heteroalkylene, $C_5$-$C_8$ cycloalkylene, $C_6$-$C_{12}$ arylene, $C_5$-$C_{14}$ heteroarylene, bivalent $C_4$-$C_{10}$ heterocycle, each of which can be optionally substituted; or
$R_1$ and $R_2'$ together form a 4- to 6-membered heterocylic ring comprising the oxygen atom adjacent to $R_1$ and the nitrogen atom adjacent to $R_2'$;
provided that the compound has at least one prodrug-forming moiety, or a residue thereof, selected from the group consisting of the first and the second prodrug-forming moieties, or residues thereof; and
X is a leaving group selected from the group consisting of halogen, cyano, hydroxyl, alkoxyl, acetate, $CF_3$—S(=O)$_2$—O—R—, tosylate, mesylate ($CH_3$—S(=O)$_2$—O—R—), nitrate (—ONO$_2$), phosphate (—OPO(OH)$_2$), carboxylate (—O—CO—R'), and phenoxide (—OAr), wherein R is alkylene or arylene, R' is alkyl or aryl, and Ar is aryl, substituted aryl, heteroaryl, or substituted heteroaryl.

In certain aspects, the presently disclosed subject matter provides a method for treating a disease or a condition, the method comprising administering to a subject in need of treatment thereof, a compound of formula (I), or a pharmaceutical composition thereof, in an amount effective for treating the disease or condition. In still other aspects, the presently disclosed subject matter provides the use of a compound of formula (I), or a pharmaceutical composition thereof, for treating a disease or condition. In some embodiments, the disease or condition is selected from the group consisting of an infection, cancer, an autoimmune disease, an inflammatory disease, and a neurodegenerative or neurological disease.

In yet another aspect, the presently disclosed subject matter provides a compound of formula (I), or a pharmaceutically composition thereof, for use as a medicament.

In yet another aspect, the presently disclosed subject matter provides a compound of formula (I), or a pharmaceutically composition thereof, for use in the treatment of a disease or condition, preferably the disease or condition is selected from the group consisting of an infection, cancer, an autoimmune disease, an inflammatory disease, and a neurodegenerative or neurological disease.

In yet another aspect, the presently disclosed subject matter provides a compound of formula (I) or a pharmaceutically composition thereof, for use in the treatment of the excess and/or aberrant glutamine activity.

Certain aspects of the presently disclosed subject matter having been stated hereinabove, which are addressed in whole or in part by the presently disclosed subject matter, other aspects will become evident as the description proceeds when taken in connection with the accompanying Examples as best described herein below.

DETAILED DESCRIPTION

The presently disclosed subject matter now will be described more fully hereinafter with reference to the accompanying FIGURES, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated FIGURES. Therefore, it is to be understood that the presently disclosed subject matter is not to be limited to the specific embodiments disclosed and that modifications and other embodiments are intended to be included within the scope of the appended claims.

I. Prodrugs of Glutamine Antagonists

Acivicin is an analog of glutamine that antagonizes a glutamine pathway. It is a fermentation product of *Streptomyces sviceus* and is an inhibitor of gamma-glutamyl transferase. Acivicin interferes with glutamate metabolism and inhibits glutamate dependent synthesis of enzymes. Accordingly, acivicin is potentially useful in the treatment of a variety of diseases. Acivicin was investigated as an anticancer agent, but trials were unsuccessful due to toxicity.

In some embodiments, the presently disclosed subject matter provides novel compositions of matter wherein promoieties have been added to acivicin. The presently disclosed prodrugs of acivicin were prepared by masking the amine and/or the carboxylate functionalities acivicin to alter its pharmacokinetics and provide slower release kinetics and cellular targeting to enhance tolerability. Further, the presently disclosed prodrugs, in some embodiments, selectively target the active glutamine antagonists to specific cells or provide a slower release of acivicin and thus decrease the toxicity of the drug molecule.

The presently disclosed subject matter demonstrates that masking both the α-amino group and the carboxy-functionality to be derivatized enhances prodrug stability and oral bioavailability. The presently disclosed prodrugs also exhibit a stability that is comparable to free acivicin.

Structures of representative acivicin prodrugs are provided in Table 1.

TABLE 1

Structures of Representative Acivicin Prodrugs

| Compound No. | Structure | MW |
|---|---|---|
| Acivicin | 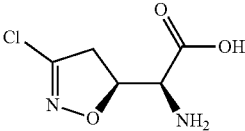 | 178.57 |
| 11 | 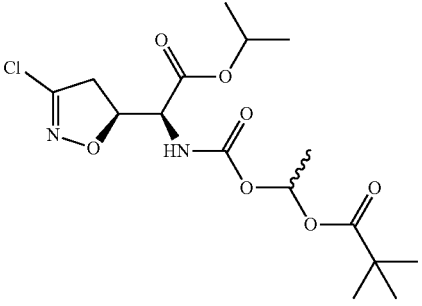 [SMILES: CC(C)OC(=O)[C@@H](NC(=O)OC(C)OC(=O)C(C)(C)C)[C@@H]1CC(Cl)=NO1] | 392.83 |
| 13 | 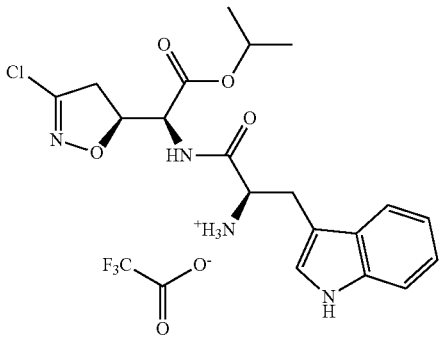 [SMILES: CC(C)OC(=O)[C@@H](NC(=O)[C@H]([NH3+])Cc1c[nH]c2ccccc12)[C@@H]1CC(Cl)=NO1 ; O=C([O-])C(F)(F)F] | 520.89 |

TABLE 1-continued

Structures of Representative Acivicin Prodrugs

| Compound No. | Structure | MW |
|---|---|---|
| 14 | 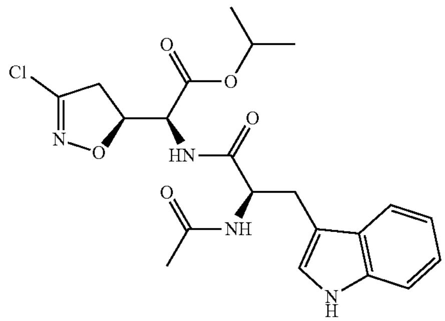 [SMILES: CC(=O)N[C@H](Cc1c[nH]c2ccccc12)C(=O)N[C@H](C(=O)OC(C)C)[C@@H]1CC(Cl)=NO1] | 448.90 |
| 16 | 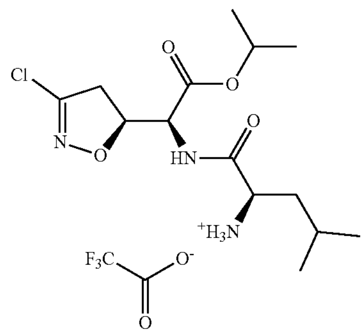 [SMILES: CC(C)C[C@@H]([NH3+])C(=O)N[C@H](C(=O)OC(C)C)[C@@H]1CC(Cl)=NO1 ; O=C([O-])C(F)(F)F] | 447.84 |
| 18 | 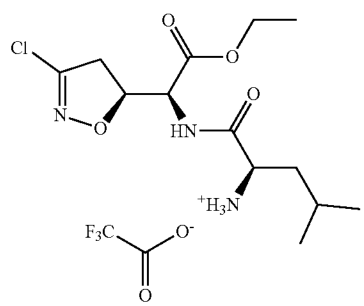 [SMILES: CCOC(=O)[C@@H](NC(=O)[C@H]([NH3+])CC(C)C)[C@@H]1CC(Cl)=NO1 ; O=C([O-])C(F)(F)F] | 433.81 |

Accordingly, in one aspect the presently disclosed subject matter provides a prodrug of acivicin, or a pharmaceutically acceptable salt or ester thereof, the prodrug having a structure of formula (I):

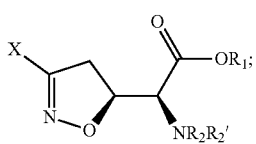

(I)

wherein:

$R_1$ is selected from the group consisting of H and a first prodrug-forming moiety, or a residue thereof, capable of forming a salt or an ester; and $R_2$ is H or a second prodrug-forming moiety, or a residue thereof, capable of forming an amide linkage, a carbamate linkage, a phosphoramidate linkage or a phosphorodiamidate linkage with the nitrogen adjacent to $R_2$;

$R_2'$ is selected from the group consisting of H, $C_1$-$C_6$ alkyl, substituted $C_1$-$C_6$ alkyl, substituted or unsubstituted succinyl (e.g., —C(=O)—CH$_2$—C—H$_2$—COOH—, wherein each —CH$_2$— group can be substituted or unsubstituted), and substituted or unsubstituted glutamyl (e.g., —C(=O)—(CH$_2$)$_2$—CH(NH$_2$)—COOH, wherein each —CH$_2$— or CH group can be substituted or unsubstituted), or $R_2$ and $R_2'$ together form a ring structure comprising —C(=O)-G-C(=O)—, wherein G is selected from the group consisting of $C_1$-$C_8$ alkylene, $C_1$-$C_8$ heteroalkylene, $C_5$-$C_8$ cycloalkylene, $C_6$-$C_{12}$ arylene, $C_5$-$C_{14}$ heteroarylene, bivalent $C_4$-$C_{10}$ heterocycle, each of which can be optionally substituted; or $R_1$ and $R_2'$ together form a 4- to 6-membered heterocylic ring comprising the oxygen atom adjacent to $R_1$ and the nitrogen atom adjacent to $R_2'$;

provided that the compound has at least one prodrug-forming moiety, or a residue thereof, selected from the group consisting of the first and the second prodrug-forming moieties, or residues thereof; and X is a leaving group selected from the group consisting of halogen, cyano, hydroxyl, alkoxyl, acetate, CF$_3$—S(=O)$_2$—O—R—, tosylate, mesylate (CH$_3$—S(=O)$_2$—O—R—), nitrate (—ONO$_2$), phosphate (—OPO(OH)$_2$), carboxylate (—O—CO—R'), and phenoxide (—OAr), wherein R is alkylene or arylene, R' is alkyl or aryl, and Ar is aryl, substituted aryl, heteroaryl, or substituted heteroaryl.

In some embodiments, R$_1$ comprises a residue of the first prodrug-forming moiety, which, together with: (i) a basic moiety and a terminal hydroxyl group forms a salt; (ii) an alkyl group and the oxygen of an adjoining hydroxyl group forms an ester; or (iii) an alkyl group and the nitrogen atom adjoining R$_2$' forms an azlactone or an oxazolidone.

In further embodiments, R$_1$ is selected from the group consisting of H, alkyl, substituted alkyl, cycloalkyl, substituted cycloalkyl, alkenyl, substituted alkenyl, alkynyl, substituted alkynyl, cycloalkenyl, substituted cycloalkenyl, alkoxyl, tri(hydrocarbyl)ammonium, and tetra(hydrocarbyl)ammonium.

In yet further embodiments, R$_1$ is selected from the group consisting of a C$_{1-6}$ straight-chain alkyl, a substituted C$_{1-6}$ straight-chain alkyl, a C$_{1-6}$ branched alkyl, a substituted C$_{1-6}$ branched alkyl, C$_{1-6}$ alkoxyl, tri(C$_1$-C$_8$-alkyl)ammonium, tetra(C$_1$-C$_8$-alkyl)ammonium, triphenylammonium, tri(hydroxy-C$_1$-C$_8$-alkyl)ammonium, and tetra(hydroxy-C$_1$-C$_8$-alkyl)ammonium, wherein each C$_1$-C$_8$ alkyl can be the same or different for each tri- or tetraammonium ion.

In yet even further embodiments, R$_1$ is selected from the group consisting of methyl, ethyl, isopropyl, ethoxyl, cyclopentyl, cyclohexyl, trimethylammonium, triethylammonium, tri(hydroxyethyl)ammonium, tripropylammonium, and tri(hydroxypropyl)ammonium.

In some embodiments, R$_2$ comprises a residue of the second prodrug-forming moiety which comprises a carbonyl, an oxy carbonyl, or a phosphonyl group, wherein the carbonyl, the oxy carbonyl, or the phosphonyl group is bound to the nitrogen of the adjoining NR$_2$' to form an amide linkage, a carbamate linkage, a phosphoramidate linkage, or a phosphorodiamidate linkage.

As used herein, a "residue" of a first or second prodrug-forming moiety includes a radical or ion of the prodrug-forming moiety that is capable of forming a bond with another part of the molecule or is capable of forming a salt or an ester.

In further embodiments, the residue of the second prodrug-forming moiety comprises a moiety selected from the group consisting of an amino acid, an N-substituted amino acid, a peptide, a substituted peptide, a monocyclic ring, a substituted monocyclic ring, a bicyclic ring, a substituted bicyclic ring, a purine nucleoside, a substituted purine nucleoside, a pyrimidine nucleoside, and a substituted pyrimidine nucleoside.

In yet further embodiments, R$_2$ is selected from the group consisting of H, alkyl, —C(=O)—Ar, —C(=O)—Y—(CR$_3$R$_4$)$_m$—Ar, —C(=O)—Y—(CR$_3$R$_4$)$_m$—NR$_5$R$_6$, —P(=O)(OR$_7$)$_n$(NHR$_9$)$_o$, —C(=O)—Y—(CR$_3$R$_4$)$_m$—Ar—O—C(=O)—R$_8$, —C(=O)—Y—(CR$_3$R$_4$)$_m$—Ar—O—R$_8$, —C(=O)—O—(CR$_3$R$_4$)$_m$—O—C(=O)—R$_{10}$, —C(=O)—O—R$_9$, —C(=O)—Y—(CR$_3$R$_4$)$_m$—Ar—O—C(=O)—Ar, and —C(=O)—Y—(CR$_3$R$_4$)$_m$—Ar—NR$_5$R$_6$; wherein: Y is —O— or a bond; m is an integer selected from the group consisting of 0, 1, 2, 3, 4, 5, 6, 7, and 8; each n and o is an integer from 0 to 2 provided that the sum of n and o is 2; each R$_3$ and R$_4$ is independently H, C$_1$-C$_6$ alkyl or substituted C$_1$-C$_6$ alkyl, aryl or substituted aryl, —(CR$_{10}$R$_{11}$)$_m$—NR$_{12}$R$_{13}$, or

[Structure: 2,3-dihydro-1H-indole with CH$_2$ substituent]

each R$_5$ and R$_6$ is independently H, alkyl, —C(=O)—(CR$_{11}$R$_{12}$)$_m$, —C(=O)—(NR$_{13}$R$_{14}$), or —C(=O)—(CR$_{11}$R$_{12}$)$_m$—NR$_{13}$R$_{14}$; each R$_7$ is independently selected from the group consisting of H, alkyl, substituted alkyl, cycloalkyl, substituted cycloalkyl, heterocyclyl, substituted heterocyclyl, alkenyl, substituted alkenyl, cycloalkenyl, substituted cycloalkenyl, —(CR$_{11}$R$_{12}$)$_m$—Z, —(CR$_{11}$R$_{12}$)$_m$-Q-Z wherein Q is a monosaccharide, aryl, substituted aryl, heteroaryl, substituted heteroaryl, and wherein Z is

[Structure: purine with NR$_{13}$R$_{14}$ substituent]

or wherein R$_7$ together with the oxygen atom to which it is attached forms a purine or pyrimidine nucleoside; each R$_8$ is independently selected from the group consisting of alkyl, substituted alkyl, cycloalkyl, substituted cycloalkyl, monosaccharide, acylated monosaccharide, aryl, substituted aryl, heteroaryl, and substituted heteroaryl; each R$_9$ is independently selected from the group consisting of H, alkyl, substituted alkyl, cycloalkyl, substituted cycloalkyl, heterocyclyl, substituted heterocyclyl, alkenyl, substituted alkenyl, cycloalkenyl, substituted cycloalkenyl, substituted aryl, heteroaryl, substituted heteroaryl, —(CR$_{11}$R$_{12}$)$_m$—Z, aryl, each R$_{10}$ is independently selected from the group consisting of alkyl, substituted alkyl, cycloalkyl, substituted cycloalkyl, monosaccharide, acylated monosaccharide, aryl, substituted aryl, heteroaryl, and substituted heteroaryl; each R$_{11}$, R$_{12}$, R$_{13}$, R$_{14}$ is independently H, C$_1$-C$_6$ alkyl or substituted C$_1$-C$_6$ alkyl, aryl or substituted aryl, and Ar is aryl, substituted aryl, heteroaryl, or substituted heteroaryl.

In particular embodiments of the compound of formula (I), R$_1$ is C$_{1-6}$ branched alkyl or C$_{1-6}$ alkoxyl, R$_2$ is —C(=O)—Y—(CR$_3$R$_4$)$_m$—NR$_5$R$_6$, wherein: Y is a bond; m=1; R$_3$ is H; R$_4$ is

[Structure: 2,3-dihydro-1H-indole with CH$_2$ substituent]

or C$_1$-C$_6$ alkyl; and R$_5$ and R$_6$ are each H.

In more particular embodiments, the compound of formula (I) is selected from the group consisting of:

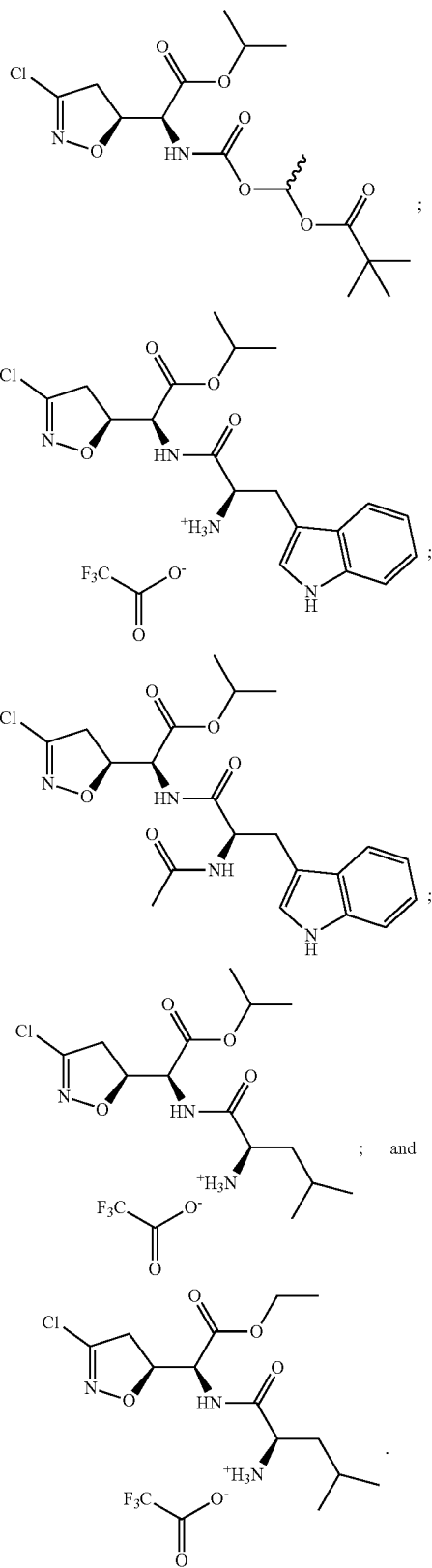

In other embodiments, the presently disclosed subject matter provides a pharmaceutical composition comprising a compound of formula (I), and a pharmaceutically acceptable carrier, diluent, or excipient.

As used herein, the term "amide linkage" comprises a structure represented by the formula:

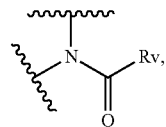

wherein $R_v$ is selected from the group consisting of alkyl, substituted alkyl, cycloalkyl, substituted cycloalkyl, aryl, substituted aryl, aralkyl, substituted aralkyl, heterocyclyl, substituted heterocyclyl, alkenyl, substituted alkenyl, cycloalkenyl, substituted cycloalkenyl, alkylamine, substituted alkylamine, heteroaryl, and substituted heteroaryl.

As used herein, the term "carbamate linkage" comprises a structure represented by the formula:

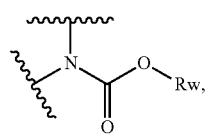

wherein $R_w$ is selected from the group consisting of alkyl, substituted alkyl, cycloalkyl, substituted cycloalkyl, aryl, substituted aryl, aralkyl, substituted aralkyl, heterocyclyl, substituted heterocyclyl, alkenyl, substituted alkenyl, cycloalkenyl, substituted cycloalkenyl, alkylamine, substituted alkylamine, heteroaryl, and substituted heteroaryl.

As used herein, the term "phosphoramidate linkage" comprises a structure represented by the formula:

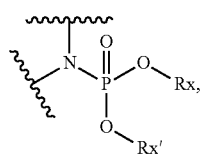

wherein $R_x$ and $R_x'$ are each independently selected from the group consisting of alkyl, substituted alkyl, cycloalkyl, substituted cycloalkyl, aryl, substituted aryl, aralkyl, substituted aralkyl, heterocyclyl, substituted heterocyclyl, alkenyl, substituted alkenyl, cycloalkenyl, substituted cycloalkenyl, alkylamine, substituted alkylamine, heteroaryl, and substituted heteroaryl.

As used herein, the term "phosphorodiamidate linkage" comprises a structure represented by the formula:

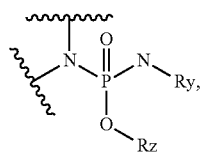

wherein $R_y$ and $R_z$ are each independently selected from the group consisting of H, alkyl, substituted alkyl, cycloalkyl, substituted cycloalkyl, heterocyclyl, substituted heterocyclyl, alkenyl, substituted alkenyl, cycloalkenyl, substituted cycloalkenyl, —(CR$_3$R$_4$)$_m$—Z, —(CR$_3$R$_4$)$_m$-Q-Z, aryl, substituted aryl, alkylamine, substituted alkylamine, heteroaryl, substituted heteroaryl, and

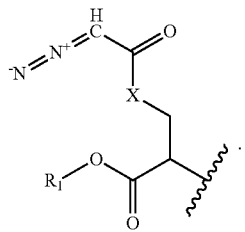

In some embodiments, X is —CH$_2$—, and n is 1.

In other embodiments, X is —O—. In some embodiments, the prodrug compound has both the first prodrug-forming moiety and the second prodrug-forming moiety, or residues thereof.

In some embodiments, R$_1$ of formula (I) comprises a residue of the first prodrug-forming moiety, which, together with a basic moiety and the terminal hydroxyl group forms a salt.

In some embodiments, R$_1$ of formula (I) comprises a residue of the first prodrug-forming moiety, which, together with an alkyl group and the oxygen of an adjoining hydroxyl group forms an ester.

In some embodiments, R$_1$ of formula (I) comprises a residue of the first prodrug-forming moiety, which, together with an alkyl group and the nitrogen adjoining the R$_2$' group, forms an azlactone or an oxazolidone.

In some embodiments, R$_1$ of formula (I) is selected from the group consisting of H, alkyl, substituted alkyl, cycloalkyl, substituted cycloalkyl, alkenyl, substituted alkenyl, alkynyl, substituted alkynyl, cycloalkenyl, substituted cycloalkenyl, tri(hydrocarbyl)ammonium, and tetra(hydrocarbyl)ammonium. Preferred alkyl group, cycloalkyl group, alkenyl group, alkynyl group, and cycloalkenyl group substituents include alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl.

In some embodiments, R$_1$ of formula (I) is not H. In some embodiments, R$_1$ of formula (I) is not H when R$_2$ and R$_2$' are H. In some embodiments, R$_2$ and R$_2$' of formula (I) are each H when and R$_1$ is not H.

In some embodiments, R$_1$ of formula (I) is selected from the group consisting of a C$_{1-6}$ straight-chain alkyl, a substituted C$_{1-6}$ straight-chain alkyl, a C$_{1-6}$ branched alkyl, a substituted C$_{1-6}$ branched alkyl, tri(C$_1$-C$_8$-alkyl)ammonium, tetra(C$_1$-C$_8$-alkyl)ammonium, triphenylammonium, tri(hydroxy-C$_1$-C$_8$-alkyl)ammonium, and tetra(hydroxy-C$_1$-C$_8$-alkyl)ammonium, wherein each C$_1$-C$_8$ alkyl can be the same or different for each tri- or tetraammonium ion.

In some embodiments, R$_1$ of formula (I) is selected from the group consisting of methyl, ethyl, isopropyl, cyclopentyl, cyclohexyl, trimethylammonium, triethylammonium, tri(hydroxyethyl)ammonium, tripropylammonium, and tri(hydroxypropyl)ammonium. In some embodiments, R$_1$ of formula (I) is methyl. In some embodiments, R$_1$ of formula (I) is ethyl. In some embodiments, R$_1$ of formula (I) is isopropyl.

In some embodiments, R$_2$ of formula (I) comprises a residue of the second prodrug-forming moiety, which, together with a carbonyl, oxy carbonyl, or phosphonyl group and the nitrogen of the adjoining NH, forms an amide, a carbamate, phosphoramidate, or phosphorodiamidate linkage.

In some embodiments, R$_2$ of formula (I) comprises a moiety selected from the group consisting of an amino acid, an N-substituted amino acid, a peptide, a substituted peptide, a monocyclic ring, a substituted monocyclic ring, a bicyclic ring, a substituted bicyclic ring, a purine nucleoside, a substituted purine nucleoside, a pyrimidine nucleoside, and a substituted pyrimidine nucleoside.

As used herein, the term "amino acid" includes moieties having a carboxylic acid group and an amino group. The term amino acid thus includes both natural amino acids (including proteinogenic amino acids) and non-natural amino acids. The term "natural amino acid" also includes other amino acids that can be incorporated into proteins during translation (including pyrrolysine and selenocysteine). Additionally, the term "natural amino acid" also includes other amino acids, which are formed during intermediary metabolism, e.g., ornithine generated from arginine in the urea cycle. The natural amino acids are summarized in Table 2:

TABLE 2

Natural Amino Acids (Used For Protein Biosynthesis)

| Amino acid | 3 letter code | 1-letter code |
| --- | --- | --- |
| Alanine | ALA | A |
| Cysteine | CYS | C |
| Aspartic Acid | ASP | D |
| Glutamic Acid | GLU | E |
| Phenylalanine | PHE | F |
| Glycine | GLY | G |
| Histidine | HIS | H |
| Isoleucine | ILE | I |
| Lysine | LYS | K |
| Leucine | LEU | L |
| Methionine | MET | M |
| Asparagine | ASN | N |
| Proline | PRO | P |
| Glutamine | GLN | Q |
| Arginine | ARG | R |
| Serine | SER | S |
| Threonine | THR | T |
| Valine | VAL | V |
| Tryptophan | TRP | W |
| Tyrosine | TYR | Y |

The natural or non-natural amino acid may be optionally substituted. In one embodiment, the amino acid is selected from proteinogenic amino acids. Proteinogenic amino acids include glycine, alanine, valine, leucine, isoleucine, aspartic acid, glutamic acid, serine, threonine, glutamine, asparagine, arginine, lysine, proline, phenylalanine, tyrosine, tryptophan, cysteine, methionine and histidine. The term amino acid includes alpha amino acids and beta amino acids, such as, but not limited to, beta alanine and 2-methyl beta alanine. The term amino acid also includes certain lactam analogues of natural amino acids, such as, but not limited to, pyroglutamine. The term amino acid also includes amino acids homologues including homocitrulline, homoarginine, homoserine, homotyrosine, homoproline and homophenylalanine.

The terminal portion of the amino acid residue or peptide may be in the form of the free acid i.e., terminating in a —COOH group or may be in a masked (protected) form, such as in the form of a carboxylate ester or carboxamide. In certain embodiments, the amino acid or peptide residue terminates with an amino group. In an embodiment, the residue terminates with a carboxylic acid group —COOH or an amino group —NH$_2$. In another embodiment, the residue terminates with a carboxamide group. In yet another embodiment, the residue terminates with a carboxylate ester.

As disclosed hereinabove, the term "amino acid" includes compounds having a —COOH group and an —NH$_2$ group. A substituted amino acid includes an amino acid which has an amino group which is mono- or di-substituted. In particular embodiments, the amino group may be mono-substituted. (A proteinogenic amino acid may be substituted at another site from its amino group to form an amino acid which is a substituted proteinogenic amino acid). The term substituted amino acid thus includes N-substituted metabolites of the natural amino acids including, but not limited to, N-acetyl cysteine, N-acetyl serine, and N-acetyl threonine.

For example, the term "N-substituted amino acid" includes N-alkyl amino acids (e.g., C$_{1-6}$ N-alkyl amino acids, such as sarcosine, N-methyl-alanine, N-methyl-glutamic acid and N-tert-butylglycine), which can include C$_{1-6}$ N-substituted alkyl amino acids (e.g., N-(carboxy alkyl) amino acids (e.g., N-(carboxymethyl)amino acids) and N-methylcycloalkyl amino acids (e.g., N-methylcyclopropyl amino acids)); N,N-di-alkyl amino acids (e.g., N,N-di-C$_{1-6}$ alkyl amino acids (e.g., N,N-dimethyl amino acid)); N,N, N-tri-alkyl amino acids (e.g., N,N,N-tri-C$_{1-6}$ alkyl amino acids (e.g., N,N,N-trimethyl amino acid)); N-acyl amino acids (e.g., C$_{1-6}$ N-acyl amino acid); N-aryl amino acids (e.g., N-phenyl amino acids, such as N-phenylglycine); N-amidinyl amino acids (e.g., an N-amidine amino acid, i.e., an amino acid in which an amine group is replaced by a guanidino group).

The term "amino acid" also includes amino acid alkyl esters (e.g., amino acid C$_{1-6}$ alkyl esters); and amino acid aryl esters (e.g., amino acid phenyl esters).

For amino acids having a hydroxy group present on the side chain, the term "amino acid" also includes O-alkyl amino acids (e.g., C$_{1-6}$ O-alkyl amino acid ethers); O-aryl amino acids (e.g., O-phenyl amino acid ethers); O-acyl amino acid esters; and O-carbamoyl amino acids.

For amino acids having a thiol group present on the side chain, the term "amino acid" also includes S-alkyl amino acids (e.g., C$_{1-6}$ S-alkyl amino acids, such as S-methyl methionine, which can include C$_{1-6}$ S-substituted alkyl amino acids and S-methylcycloalkyl amino acids (e.g., S-methylcyclopropyl amino acids)); S-acyl amino acids (e.g., a C$_{1-6}$ S-acyl amino acid); S-aryl amino acid (e.g., a S-phenyl amino acid); a sulfoxide analogue of a sulfur-containing amino acid (e.g., methionine sulfoxide) or a sulfoxide analogue of an S-alkyl amino acid (e.g., S-methyl cystein sulfoxide) or an S-aryl amino acid.

In other words, the presently disclosed subject matter also envisages derivatives of natural amino acids, such as those mentioned above which have been functionalized by simple synthetic transformations known in the art (e.g., as described in "Protective Groups in Organic Synthesis" by T W Greene and P G M Wuts, John Wiley & Sons Inc. (1999)), and references therein.

Examples of non-proteinogenic amino acids include, but are not limited to: citrulline, hydroxyproline, 4-hydroxyproline, β-hydroxyvaline, ornithine, β-amino alanine, albizziin, 4-amino-phenylalanine, biphenylalanine, 4-nitro-phenylalanine, 4-fluoro-phenylalanine, 2,3,4,5,6-pentafluoro-phenylalanine, norleucine, cyclohexylalanine, α-aminoisobutyric acid, α-aminobutyric acid, α-aminoisobutyric acid, 2-aminoisobutyric acid, 2-aminoindane-2-carboxylic acid, selenomethionine, lanthionine, dehydroalanine, γ-amino butyric acid, naphthylalanine, aminohexanoic acid, pipecolic acid, 2,3-diaminoproprionic acid, tetrahydroisoquinoline-3-carboxylic acid, tert-leucine, tert-butylalanine, cyclopropylglycine, cyclohexylglycine, 4-aminopiperidine-4-carboxylic acid, diethylglycine, dipropylglycine and derivatives thereof wherein the amine nitrogen has been mono- or di-alkylated.

The term "peptide" refers to an amino acid chain consisting of 2 to 9 amino acids, unless otherwise specified. In preferred embodiments, the peptide used in the present invention is 2 or 3 amino acids in length. In one embodiment, a peptide can be a branched peptide. In this embodiment, at least one amino acid side chain in the peptide is bound to another amino acid (either through one of the termini or the side chain).

The term "N-substituted peptide" refers to an amino acid chain consisting of 2 to 9 amino acids in which one or more NH groups are substituted, e.g., by a substituent described elsewhere herein in relation to substituted amino groups. Optionally, the N-substituted peptide has its N-terminal amino group substituted and, in one embodiment, the amide linkages are unsubstituted.

In one embodiment, an amino acid side chain is bound to another amino acid. In a further embodiment, side chain is bound to the amino acid via the amino acid's N-terminus, C-terminus, or side chain.

Examples of natural amino acid sidechains include hydrogen (glycine), methyl (alanine), isopropyl (valine), sec-butyl (isoleucine), —CH$_2$CH(CH$_3$)$_2$(leucine), benzyl (phenylalanine), p-hydroxybenzyl (tyrosine), —CH$_2$OH (serine), —CH(OH)CH$_3$ (threonine), —CH$_2$-3-indoyl (tryptophan), —CH$_2$COOH (aspartic acid), CH$_2$CH$_2$COOH (glutamic acid), —CH$_2$C(O)NH$_2$ (asparagine), —CH$_2$CH$_2$C(O)NH$_2$ (glutamine), —CH$_2$SH, (cysteine), —CH$_2$CH$_2$SCH$_3$ (methionine), —(CH$_2$)$_4$NH$_2$ (lysine), —(CH$_2$)$_3$NHC(=NH) NH$_2$ (arginine) and —CH$_2$-3-imidazoyl (histidine).

Exemplary monocyclic rings and bicyclic rings include, without limitation, benzene, pyrimidines, and purines, and more generally aryl and heteroaryl rings. Exemplary heteroaryls include, but are not limited to, pyridyl, pyrimidinyl, pyrazinyl, furanyl, thienyl, pyrazolyl, oxazolyl, thiazolyl, isothiazolyl, isoxazolyl, pyrrolyl, imidazolyl, indolyl, indolinolyl, and imidazopyridazinyl. Aryls include phenyl (C$_6$), benzyl, naphthyl (C$_{10}$), and biphenyl (C$_{12}$). Exemplary pyrimidines include, without limitation, cytosine, thymine, and uracil. Exemplary purines include, without limitation, purine, adenine, N-substituted adenine, guanine, hypoxanthine, xanthine, theobromine, caffeine, uric acid, and isoguanine. Exemplary purine nucleosides include, without limitation, adenine and guanine.

As used herein, an "amino acid residue," refers to amino acid structures that lack a hydrogen atom of the amino group, e.g., —NH—CHR—COOH, or the hydroxyl moiety of the carboxyl group, e.g., NH$_2$—CHR—CO—, or both, e.g., —NH—CHR—COO—. For example, when two or more amino acids combine to form a peptide, the elements of water are removed and what remains of each amino acid is called an amino-acid residue. Therefore, all units of a peptide chain are amino-acid residues. The residue in a peptide that has an amino group that is free, or at least not acylated by another amino-acid residue (it may, for example, be acylated or formylated), is called N-terminal; it is at the N-terminus. The residue that has a free carboxyl group, or at least does not acylate another amino-acid residue, (it may, for example, acylate ammonia to give —NH—CHR—CO—NH$_2$), is called C-terminal.

Further, it should be appreciated that a terminal carboxy group of the compounds of formula (I) can be used to form salts. In an exemplary embodiment, a salt of any of the compounds of formula (I) shown above can be formed when an H is replaced by NEt$_3$, as will be appreciated by those skilled in the art.

II. Pharmaceutical Compositions and Administration

In another aspect, the present disclosure provides a pharmaceutical composition including one prodrug compound of formula (I), alone or in combination with one or more additional therapeutic agents in admixture with a pharmaceutically acceptable excipient. Accordingly, in some embodiments, the presently disclosed subject matter provides a pharmaceutical composition comprising a compound of formula (I), and a pharmaceutically acceptable carrier, diluent, or excipient. One of skill in the art will recognize that the pharmaceutical compositions include the pharmaceutically acceptable salts of the compounds described above.

Pharmaceutically acceptable salts are generally well known to those of ordinary skill in the art, and include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent or by ion exchange, whereby one basic counterion (base) in an ionic complex is substituted for another. Examples of pharmaceutically acceptable base addition salts include sodium, potassium, calcium, ammonium, organic amino, or magnesium salt, or a similar salt.

When compounds of the present disclosure contain relatively basic functionalities, acid addition salts can be obtained by contacting the neutral form of such compounds with a sufficient amount of the desired acid, either neat or in a suitable inert solvent or by ion exchange, whereby one acidic counterion (acid) in an ionic complex is substituted for another. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-toluenesulfonic, citric, tartaric, methanesulfonic, and the like. Also included are salts of amino acids, such as arginate and the like, and salts of organic acids like glucuronic or galactunoric acids and the like (see, for example, Berge et al, "Pharmaceutical Salts," Journal of Pharmaceutical Science, 1977, 66, 1-19). Certain specific compounds of the present disclosure contain both basic and acidic functionalities that allow the compounds to be converted into either base or acid addition salts.

Accordingly, pharmaceutically acceptable salts suitable for use with the presently disclosed subject matter include, by way of example but not limitation, acetate, benzenesulfonate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy (20$^{th}$ ed.) Lippincott, Williams & Wilkins (2000).

In particular embodiments, the salt is a tri(hydrocarbyl)ammonium or tetra(hydrocarbyl)ammonium salt. In yet more particular embodiments, the salt is selected from the group consisting of a tri($C_1$-$C_8$-alkyl)ammonium, tetra($C_1$-$C_8$-alkyl)ammonium, triphenylammonium, tri(hydroxy-$C_1$-$C_8$-alkyl)ammonium, and tetra(hydroxy-$C_1$-$C_8$-alkyl)ammonium salt, wherein each $C_1$-$C_8$ alkyl can be the same or different for each tri- or tetraammonium ion. In even more particular embodiments, the salt is selected from the group consisting of a trimethylammonium, triethylammonium, tri(hydroxyethyl)ammonium, tripropylammonium, and tri(hydroxypropyl)ammonium salt.

In therapeutic and/or diagnostic applications, the compounds of the disclosure can be formulated for a variety of modes of administration, including oral (sublingual, buccal), peroral, sublingual, systemic and topical or localized administration. Techniques and formulations generally may be found in Remington: The Science and Practice of Pharmacy (20$^{th}$ ed.) Lippincott, Williams & Wilkins (2000).

Depending on the specific conditions being treated, such agents may be formulated into liquid (e.g., solutions, suspensions, or emulsions) or solid dosage forms (capsules or tablets) and administered systemically or locally. The agents may be delivered, for example, in a timed-, controlled-, or sustained-slow release form as is known to those skilled in the art. Techniques for formulation and administration may be found in Remington: The Science and Practice of Pharmacy (20$^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intra-sternal, intra-synovial, intra-hepatic, intralesional, intracranial, intraperitoneal, intranasal, or intraocular injections or other modes of delivery. In some embodiments, the pharmaceutical composition is administered orally. In some embodiments, the pharmaceutical composition is administered intravenously. In some embodiments, the pharmaceutical composition is administered intramuscularly. In some embodiments, the pharmaceutical composition is administered intrathecally. In some embodiments, the pharmaceutical composition is administered subcutaneously.

For injection, the agents of the disclosure may be formulated and diluted in aqueous solutions, such as in physiologically compatible buffers, such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances, such as saline; preservatives, such as benzyl alcohol; absorption promoters; and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein. Generally, the compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, the bioavailability of the compound(s), the adsorption, distribution, metabolism, and excretion (ADME) toxicity of the compound(s), and the preference and experience of the attending physician.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers, such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof, such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler, such as lactose, binders, such as starches, and/or lubricants such, as talc or magnesium stearate, optionally, stabilizers. In soft capsules, the active compounds may be dissolved or suspended in suitable liquids, such as fatty oils, liquid paraffin, or liquid polyethylene glycols (PEGs). In addition, stabilizers may be added.

III. Methods for Treating a Disease or Disorder

The presently disclosed compounds are, which are orally bioavailable, less toxic prodrugs of glutamine analogs that are glutamine antagonists, allow a clinically acceptable dosing paradigm for diseases or conditions wherein excess and/or aberrant glutamine activity is implicated. As used herein, the term "glutamine antagonist" refers to a glutamine analog that interferes with a glutamine metabolic pathway, e.g., the inhibition or blocking of a metabolic pathway downstream of glutamine in which glutamine acts as a precursor of one or more non-glutamine compounds. Examples of such metabolic pathways are well known (see, e.g., Hensley et al., "Glutamine and cancer: cell biology, physiology, and clinical opportunities" *J Clin Invest.* 2013; 123(9):3678-3684; DeBerardinis et al., "Q's next: the diverse functions of glutamine in metabolism, cell biology and cancer" *Oncogene.* 2009; 29(3):313-324; and Medina et al., "Relevance of glutamine metabolism to tumor cell growth" *Mol Cell Biochem.* 1992; 113(1):1-15). In some contexts, the term glutamine antagonist also includes glutamine analogs that inhibit glutamine uptake by cells, thereby reducing its biological activity. Diseases or conditions wherein excess and/or aberrant glutamine activity is implicated include, but are not limited to, infection, cancer, autoimmune diseases, and neurodegenerative or neurological diseases and other central nervous system disorders. In particular embodiments, the glutamine antagonist is acivicin.

In general, the presently disclosed methods result in a decrease in the severity of a disease or condition in a subject. The term "decrease" is meant to inhibit, suppress, attenuate, diminish, arrest, or stabilize a symptom of a disease or condition.

As used herein, the terms "treat," "treating," "treatment," and the like refer to reducing or ameliorating a disease or condition, and/or symptoms associated therewith. It will be appreciated that, although not precluded, treating a disease or condition does not require that the disorder, condition or symptoms associated therewith be completely eliminated.

Accordingly, in some embodiments, the presently disclosed subject matter provide a method for treating a disease or a condition, the method comprising administering to a subject in need of treatment thereof, a compound of formula (I), or a pharmaceutical composition of any thereof, in an amount effective for treating the disease or condition.

The presently disclosed subject matter contemplates using a prodrug of formula (I), or a pharmaceutical composition comprising the prodrug of formula (I), optionally together with at least one antimicrobial agent (e.g., antibiotic, antiviral, and the like), to treat an infection.

As used herein, "infection" refers to the invasion of a host organism's bodily tissues by disease-causing organisms, their multiplication, and the reaction of host tissues to these organisms and the toxins they produce. Infectious disease, such as infection by any bacteria or virus, is contemplated for treatment using a compound of formula (I), or a pharmaceutical composition of any thereof.

In some embodiments, the infection comprises a bacterial infection. In some embodiments, the compound of formula (I), or pharmaceutical composition of any thereof, inhibits bacterial growth and/or survival.

In some embodiments, the infection comprises a viral infection. Examples of viral infections contemplated for treatment using a compound of formula (I), or a pharmaceutical composition of any thereof include, without limitation, herpes simplex virus type 1 (HSV-1), herpes simplex virus type 2 (HSV-2), human cytomegalovirus (HCMV), human parainfluenza virus type 2 (HPIV-2), Maloney leukemia virus (MLV), mumps, paramyxovirus, poliovirus, reovirus type 3, respiratory syncytial virus (RSV), Sendai virus, and vesicular stomatitis virus (VSV).

In some embodiments, the compound of formula (I), or pharmaceutical composition of any thereof, inhibits viral replication. In some embodiments, the compound of formula (I), or pharmaceutical composition of any thereof, inhibits replication of herpes simplex virus type 1 (HSV-1). In some embodiments, the compound of formula (I), or pharmaceutical composition of any thereof, inhibits replication of herpes simplex virus type 2 (HSV-2). In some embodiments, the compound of formula (I), or pharmaceutical composition of any thereof, inhibits replication of human cytomegalovirus (HCMV). In some embodiments, the compound of formula (I), or pharmaceutical composition of any thereof, inhibits replication of human parainfluenza virus type 2 (HPIV-2). In some embodiments, the compound of formula (I), or pharmaceutical composition of any thereof, inhibits replication of Maloney leukemia virus (MLV). In some embodiments, the compound of formula (I), or pharmaceutical composition of any thereof, inhibits replication of mumps. In some embodiments, the compound of formula (I), or pharmaceutical composition of any thereof, inhibits replication of paramyxovirus. In some embodiments, the compound of formula (I), or pharmaceutical composition of any thereof, inhibits replication of poliovirus. In some embodiments, the compound of formula (I), or pharmaceutical composition of any thereof, inhibits replication of reovirus type 3. In some embodiments, the compound of formula (I), or pharmaceutical composition of any thereof, inhibits replication of respiratory syncytial virus (RSV). In some embodiments, the compound of formula (I), or pharmaceutical composition of any thereof, inhibits replication of Sendai virus. In some embodiments, the compound of formula (I), or pharmaceutical composition of any thereof, inhibits replication of vesicular stomatitis virus (VSV).

In some embodiments, the viral infection is influenza. As used herein, "influenza" refers to influenza A, B, or C, parainfluenza viruses, and any other influenza-like virus.

In an aspect, the presently disclosed subject matter involves the use of a compound of formula (I), or a pharmaceutical composition thereof, optionally together with an antiviral agent, for the manufacture of a medicament for treating a viral infection and/or inhibiting replication.

As used herein, "antiviral agent" includes a compound that inhibits the replication of viruses in cells, tissues, or organisms. Examples of antiviral agents contemplated for use in combination with a prodrug of formula (I), or a pharmaceutical composition comprising a prodrug of formula (I) include, but are not limited to, Acyclovir (2-amino-1,9-dihydro-9-[(2-hydroxyethoxy)methyl]-6H-purin-6-one), Valacyclovir (L-valine, 2-[(2-amino-1,6-dihydro-6-oxo-9H-purin-9-yl)methoxy]ethyl ester, Pencyclovir (9-[4-hydroxy-3-(hydroxymethylbutyl)]guanine), Famcyclovir (2-[2-(amino-9H-purin-9-yl)]ethyl-1,3-propanediol diacetate), Ribavirin (1-beta-D-ribofuanosyl-1-H-1,2,4-triazol-3-carboxamide), Lamivudine ((2R,cis)-4-amino-1-(2-hydroxymethyl-1,3-oxathiolan-5-yl)-(1H)-pyrimidine-2-one), Amantadine (1-amantanamine hydrochloride), and Rimantadine (α-methyltricyclo (3.3.1.1/3.7 decane-1-methylamine hydrochloride).

The presently disclosed subject matter contemplates using a prodrug of formula (I), or a pharmaceutical composition comprising the prodrug of formula (I), optionally together with at least one chemotherapeutic agent, at least one radiotherapeutic agent, and/or at least one immunotherapeutic agent to treat cancer. In some embodiments, such treatment includes treatment with any combination of radiotherapy, immunotherapy, photodynamic therapy, proton therapy, and/or surgery.

A "chemotherapeutic agent" is used to connote a compound or composition that is administered in the treatment of cancer. Chemotherapeutic agents contemplated for use in combination with a prodrug of formula (I), or a pharmaceutical composition comprising a prodrug of formula (I) include, but are not limited to, alkylating agents, such as thiotepa and cyclophosphamide; alkyl sulfonates, such as busulfan, improsulfan and piposulfan; aziridines, such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas, such as carmustine, chlorozotocin, fotemustine, lomustine, nimustine, ranimustine; antibiotics, such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, such as methotrexate and 5-fluorouracil (5-FU); folic acid analogues, such as denopterin, methotrexate, pteropterin, trimetrexate; purine analogs, such as fludarabine, 6-mercaptopurine, thiamiprine, thioguanine; pyrimidine analogs, such as ancitabine, azacitidine, 6-azauridine, carmofur, cytosine arabinoside, dideoxyuridine, doxifluridine, enocitabine, floxuridine, 5-FU; androgens, such as calusterone, dromostanolone propionate, epitiostanol, mepitiostane, testolactone; anti-adrenals, such as aminoglutethimide, mitotane, trilostane; folic acid replenishers, such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); taxoids, e.g., paclitaxel and docetaxel; chlorambucil; gemcitabine; 6-thioguanine; mercaptopurine; platinum analogs, such as cisplatin and carboplatin; vinblastine; platinum; etoposide; ifosfamide; mitomycin C; mitoxantrone; vincristine; vinorelbine; navelbine; novantrone; teniposide; daunomycin; aminopterin; xeloda; ibandronate; CPT11; topoisomerase inhibitor RFS 2000; difluoromethylornithine; retinoic acid; esperamicins;

capecitabine; and pharmaceutically acceptable salts, acids or derivatives of any of the above. Chemotherapeutic agents also include anti-hormonal agents that act to regulate or inhibit hormone action on tumors, such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens, such as flutamide, nilutamide, bicalutamide, leuprolide, and goserelin; and pharmaceutically acceptable salts, acids or derivatives of any of the above.

In some embodiments, the chemotherapeutic agent is a topoisomerase inhibitor. Topoisomerase inhibitors are chemotherapy agents that interfere with the action of a topoisomerase enzyme (e.g., topoisomerase I or II). Topoisomerase inhibitors include, but are not limited to, doxorubicin HCl, daunorubicin citrate, mitoxantrone HCl, actinomycin D, etoposide, topotecan HCl, teniposide, and irinotecan, as well as pharmaceutically acceptable salts, acids, or derivatives of any of these.

In some embodiments, the chemotherapeutic agent is an anti-metabolite. An anti-metabolite is a chemical with a structure that is similar to a metabolite required for normal biochemical reactions, yet different enough to interfere with one or more normal functions of cells, such as cell division. Anti-metabolites include, but are not limited to, gemcitabine, fluorouracil, capecitabine, methotrexate sodium, ralitrexed, pemetrexed, tegafur, cytosine arabinoside, thioguanine, 5-azacytidine, 6-mercaptopurine, azathioprine, 6-thioguanine, pentostatin, fludarabine phosphate, and cladribine, as well as pharmaceutically acceptable salts, acids, or derivatives of any of these.

In certain embodiments, the chemotherapeutic agent is an antimitotic agent, including, but not limited to, agents that bind tubulin. In some embodiments, the agent is a taxane. In certain embodiments, the agent is paclitaxel or docetaxel, or a pharmaceutically acceptable salt, acid, or derivative of paclitaxel or docetaxel. In certain alternative embodiments, the antimitotic agent comprises a vinca alkaloid, such as vincristine, binblastine, vinorelbine, or vindesine, or pharmaceutically acceptable salts, acids, or derivatives thereof.

As used herein, the term "immunotherapeutic agent" refers to a molecule that can aid in the treatment of a disease by inducing, enhancing, or suppressing an immune response in a cell, tissue, organ or subject. Examples of immunotherapeutic agents contemplated for use in combination with a prodrug of formula (I), or a pharmaceutical composition comprising a prodrug of formula (I) include, but are not limited to, immune checkpoint molecules (e.g., antibodies to immune checkpoint proteins), interleukins (e.g., IL-2, IL-7, IL-12, IL-15), cytokines (e.g., interferons, G-CSF, imiquimod), chemokines (e.g., CCL3, CCL26, CXCL7), vaccines (e.g., peptide vaccines, dendritic cell (DC) vaccines, EGFRvIII vaccines, mesothilin vaccine, G-VAX, listeria vaccines), and adoptive T cell therapy including chimeric antigen receptor T cells (CAR T cells).

As used herein, "radiotherapeutic agent" means an agent which may be used in radiotherapy that acts through damaging cells (e.g., malignant cells) as a target through radiation irradiation. An exemplary radiotherapeutic agent contemplated for use in combination with a prodrug of formula (I), or a pharmaceutical composition comprising a prodrug of formula (I) is the titanium peroxide contained in the substrate particle which generates a hydroxyl radial through radiation irradiation, and the hydroxyl radial exerts an action of attacking a target, as described in U.S. Publication No. 2013/0017266, which is incorporated by reference herein in its entirety.

As used herein, a "cancer" in a patient refers to the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. In some circumstances, cancer cells will be in the form of a tumor; such cells may exist locally within an animal, or circulate in the blood stream as independent cells, for example, leukemic cells. A "tumor," as used herein, refers to all neoplastic cell growth and proliferation, whether malignant or benign, and all precancerous and cancerous cells and tissues. A "solid tumor," as used herein, is an abnormal mass of tissue that generally does not contain cysts or liquid areas. A solid tumor may be in the brain, colon, breasts, prostate, liver, kidneys, lungs, esophagus, head and neck, ovaries, cervix, stomach, colon, rectum, bladder, uterus, testes, and pancreas, as non-limiting examples. In some embodiments, the solid tumor regresses or its growth is slowed or arrested after the solid tumor is treated with the presently disclosed methods. In other embodiments, the solid tumor is malignant. In some embodiments, the cancer comprises Stage 0 cancer. In some embodiments, the cancer comprises Stage I cancer. In some embodiments, the cancer comprises Stage II cancer. In some embodiments, the cancer comprises Stage III cancer. In some embodiments, the cancer comprises Stage IV cancer. In some embodiments, the cancer is refractory and/or metastatic. For example, the cancer may be refractory to treatment with radiotherapy, chemotherapy or monotreatment with immunotherapy. Cancer as used herein includes newly diagnosed or recurrent cancers, including without limitation, acute lymphoblastic leukemia, acute myelogenous leukemia, advanced soft tissue sarcoma, brain cancer, metastatic or aggressive breast cancer, breast carcinoma, bronchogenic carcinoma, choriocarcinoma, chronic myelocytic leukemia, colon carcinoma, colorectal carcinoma, Ewing's sarcoma, gastrointestinal tract carcinoma, glioma, glioblastoma multiforme, head and neck squamous cell carcinoma, hepatocellular carcinoma, Hodgkin's disease, intracranial ependymoblastoma, large bowel cancer, leukemia, liver cancer, lung carcinoma, Lewis lung carcinoma, lymphoma, malignant fibrous histiocytoma, a mammary tumor, melanoma, mesothelioma, neuroblastoma, osteosarcoma, ovarian cancer, pancreatic cancer, a pontine tumor, premenopausal breast cancer, prostate cancer, rhabdomyosarcoma, reticulum cell sarcoma, sarcoma, small cell lung cancer, a solid tumor, stomach cancer, testicular cancer, and uterine carcinoma.

In some embodiments, the cancer is acute leukemia. In some embodiments, the cancer is acute lymphoblastic leukemia. In some embodiments, the cancer is acute myelogenous leukemia. In some embodiments, the cancer is advanced soft tissue sarcoma. In some embodiments, the cancer is a brain cancer. In some embodiments, the cancer is breast cancer (e.g., metastatic or aggressive breast cancer). In some embodiments, the cancer is breast carcinoma. In some embodiments, the cancer is bronchogenic carcinoma. In some embodiments, the cancer is choriocarcinoma. In some embodiments, the cancer is chronic myelocytic leukemia. In some embodiments, the cancer is a colon carcinoma (e.g., adenocarcinoma). In some embodiments, the cancer is colorectal cancer (e.g., colorectal carcinoma). In some embodiments, the cancer is Ewing's sarcoma. In some embodiments, the cancer is gastrointestinal tract carcinoma. In some embodiments, the cancer is a glioma. In some embodiments, the cancer is glioblastoma multifome. In some embodiments, the cancer is head and neck squamous cell carcinoma. In some embodiments, the cancer is hepatocellular carcinoma. In some embodiments, the cancer is Hodgkin's disease. In some embodiments, the cancer is intracranial ependymoblastoma. In some embodiments, the cancer is large bowel cancer. In some embodiments, the cancer is leukemia. In some embodiments, the cancer is liver cancer. In some embodiments, the cancer is lung cancer (e.g., lung carcinoma). In some embodiments, the cancer is Lewis lung carcinoma. In some embodiments, the cancer is lymphoma. In some embodiments, the cancer is malignant fibrous histiocytoma. In some embodiments, the cancer comprises a mammary tumor. In some embodiments, the cancer is melanoma. In some embodiments, the cancer is mesothelioma. In some embodiments, the cancer is neuroblastoma. In some embodiments, the cancer is osteosarcoma. In some embodiments, the cancer is ovarian cancer. In some embodiments, the cancer is pancreatic cancer. In some embodiments, the cancer comprises a pontine tumor. In some embodiments, the cancer is premenopausal breast cancer. In some embodiments, the cancer is prostate cancer. In some embodiments, the cancer is rhabdomyosarcoma. In some embodiments, the cancer is reticulum cell sarcoma. In some embodiments, the cancer is sarcoma. In some embodiments, the cancer is small cell lung cancer. In some embodiments, the cancer comprises a solid tumor. In some embodiments, the cancer is stomach cancer. In some embodiments, the cancer is testicular cancer. In some embodiments, the cancer is uterine carcinoma.

In some embodiments, the cancer comprises a glutamine-dependent cancer in which glutamine is an important fuel source for cellular energy in the cancer (e.g., hematopoietic tumors, hepatomas, Ehrlich carcinoma (see Huber et al., "Uptake of glutamine antimetabolites 6-diazo-5-oxo-L-norleucine (DON) in sensitive and resistant tumor cell lines," *Int. J. Cancer.* 1988; 41:752-755)).

In some embodiments, the cancer is a Myc-dependent cancer. As used herein, "Myc-dependent cancer" refers to a cancer exhibiting activation, overexpression and/or amplification of c-Myc. In some contexts, a "Myc-dependent cancer" is a cancer in which c-Myc plays a role in increased glutamine metabolism in the cancer cells. Examples of Myc-dependent cancers include, without limitation, lymphoma, neuroblastoma, and small cell lung cancer.

In some embodiments, the cancer is an mTORC1-dependent cancer. As used herein, "mTORC1-dependent cancer" refers to a cancer in which mTORC1 is activated in a glutamine-dependent manner, i.e., that is mTORC1 plays a role in increased glutamine metabolism in the cancer cells.

The presently disclosed subject matter contemplates using a prodrug of formula (I), or a pharmaceutical composition comprising the prodrug of formula (I), optionally together with at least one immunosuppressant and/or anti-inflammatory agent, to treat an autoimmune disease, immune disorder, or inflammatory disorder.

As used herein, "immunosuppressant agent" means an agent which may be used in immunotherapy to reduce or prevent an immune response in a cell, organ, tissue, or subject. Examples of immunosuppressant agents contemplated for use in combination with a prodrug of formula (I), or a pharmaceutical composition comprising a prodrug of formula (I) include corticosteriods, calcineurin inhibitors, antiproliferative agents, SIP receptor agonists, kinase inhibitors, monoclonal antilymphocyte antibodies and polyclonal antilymphocyte antibodies. Non-limiting examples of corticosteroids include Prednisone (Deltasone® and Orasone®) and Methylprednisolone (SoluMedrol®). Non-limiting examples of calcineurin inhibitors include Cyclosporine (Cyclosporin A, SangCya, Sandimmune®, Neoral®, Gengraf®), ISA, Tx247, ABT-281, ASM 981 and Tacrolimus (Prograf®, FK506). Non-limiting examples of antiproliferative agents include Mycophenolate Mofetil (CellCept®), Azathioprene (Imuran®), and Sirolimus (Rapamune®). Non-limiting examples of SIP receptor agonists include FTY 720 or analogues thereof. Non-limiting examples of kinase inhibitors include mTOR kinase inhibitors, which are compounds, proteins or antibodies that target, decrease or inhibit the activity and/or function of members of the serine/threonine mTOR family. These include, without limitation, CCI-779, ABT578, SAR543, rapamycin and derivatives or analogs thereof, including 40-O-(2-hydroxyethyl)-rapamycin, rapalogs, including AP23573, AP23464, AP23675 and AP23841 from Ariad, Everolimus (CERTICAN, RAD001), biolimus 7, biolimus 9 and sirolimus (RAPAMUNE). Kinase inhibitors also include protein kinase C inhibitors, which include the compounds described the PCT publications WO 2005/097108 and WO 2005/068455, which are herein incorporated by reference in their entireties. Non-limiting examples of monoclonal antilymphocyte antibodies include Muromonab-CD3 (Orthoclone OKT3®), Interleukin-2 Receptor Antagonist (Basiliximab, Simulect®), and Daclizumab (Zenapax®). Non-limiting examples of polyclonal antilymphocyte antibodies include Antithymocyte globulin-equine (Atgam®) and Antithymocyte globulin-rabbit (RATG, Thymoglobulin®). Other immunosuppressants include, without limitation, SERP-1, a serine protease inhibitor produced by malignant rabbit fibroma virus (MRV) and myxoma virus (MYX), described in US Patent Publication No. 2004/0029801, which is incorporated herein by reference.

As used herein, "anti-inflammatory agent" refers to an agent that may be used to prevent or reduce an inflammatory response or inflammation in a cell, tissue, organ, or subject. Exemplary anti-inflammatory agents contemplated for use in combination with a prodrug of formula (I), or a pharmaceutical composition comprising a prodrug of formula (I) include, without limitation, steroidal anti-inflammatory agents, a nonsteroidal anti-inflammatory agent, or a combination thereof. In some embodiments, anti-inflammatory agents include clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone, dexamethasone acetate, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof. The anti-inflammatory agent may also be a biological inhibitor of proinflammatory signaling molecules including antibodies to such biological inflammatory signaling molecules.

Autoimmunity is the failure of an organism to recognize its own constituent parts (down to the sub-molecular levels) as "self," which results in an immune response against its own cells and tissues. Any disease that results from such an aberrant immune response is termed an autoimmune disease. An unwanted immune response may be, for example, immune responses associated with an autoimmune disorder, allergies, or inflammatory disorders. The term "immune disorders" are diseases involving the immune system that can include but not be limited to allergies, autoimmune diseases, immune complex diseases, immunodeficiency diseases and cancers of the immune system. In some embodiments, the autoimmune disease, immune disorder, or inflammatory disorder is multiple sclerosis.

The presently disclosed subject matter contemplates using a prodrug of formula (I), or a pharmaceutical composition comprising the prodrug of formula (I), optionally together with at least one neuroprotective agent and/or at least one neurotrophic factor, and/or at least one neuroregenerative agent, to treat a neurodegenerative or neurological disorder or disease.

A "neurodegenerative disorder" is a disease, disorder, or condition that is characterized by the progressive loss of the structure or function of neurons (e.g., degeneration or dysfunction of neurons or other neural cells). Glutaminase-catalyzed hydrolysis of glutamine to glutamate is a predominant source of brain glutamate. Normal central nervous system (CNS) synaptic transmission uses glutamate as the major excitatory amino acid neurotransmitter. Excessive glutamatergic signaling, known as excitotoxicity, is believed to cause CNS damage in various neurodegenerative diseases, such as stroke, amyotrophic lateral sclerosis (ALS), Huntington's disease, Alzheimer's disease, and HIV-associated dementia. Accordingly, without wishing to be bound by theory, it is believed that the presently disclosed prodrugs can be used to treat such neurodegenerative diseases, for example, by inhibiting glutaminase to ameliorate the CNS damage resulting from excitotoxicity due to excessive glutamatergic signaling.

In particular embodiments, the neurodegenerative disorder is multiple sclerosis (MS). In particular embodiments, the neurodegenerative disorder is HIV-associated dementia (HAD). In particular embodiments, the neurodegenerative disorder is ischemia (e.g., transient ischemic brain injury). In particular embodiments, the neurodegenerative disorder is stroke. In particular embodiments, the neurodegenerative disorder is amyotrophic lateral sclerosis (ALS). In particular embodiments, the neurodegenerative disorder is Huntington's disease. In particular embodiments, the neurodegenerative disorder is Alzheimer's disease.

In some embodiments, the presently disclosed subject matter provides methods for inhibiting the excess and/or aberrant glutamine activity found in a subject with a disease or condition. As used herein, the term "inhibit" means to decrease or diminish the excess and/or aberrant glutamine activity found in a subject. The term "inhibit" also may mean to decrease, suppress, attenuate, diminish, arrest, or stabilize the development or progression of a disease or condition. Inhibition may occur, for e.g., by at least 10%, 20%, 30%, 40%, 50%, 60%, 70%, 80%, 90%, 95%, 98%, 99%, or even 100% compared to an untreated control subject or a subject without the disease or disorder. As used herein, the term "excess glutamine activity" means an increase in glutamine activity in a subject with a disease or condition as compared to the glutamine activity in a subject without a similar disease or condition, such as an increase of approximately 100%, 100%, 200%, 300%, 400%, 500%, 600%, 700%, 800%, 900%, 1000%, or more. As used herein, the term "aberrant glutamine activity" means a change in the biological activity of glutamine in a subject with a disease or condition as compared to the glutamine activity in a subject without a similar disease or condition, such utilization of glutamine in the growth and/or proliferation of malignant, neoplastic, or other pathologic cellular processes.

In some embodiments, the disease or condition involves excess and/or aberrant glutamine activity. In such aspects, the method further comprises inhibiting the excess and/or aberrant glutamine activity when the compound of formula (I), or the pharmaceutical composition of any thereof, is administered.

In another aspect, the presently discloses subject matter involves the use of a compound of formula (I), or a pharmaceutical composition of any thereof, for treating a disease or condition. In some embodiments, the compound of formula (I), or the pharmaceutical composition of any thereof is used to treat a disease or condition selected from the group consisting of an infection, cancer, an autoimmune disease, an inflammatory disease, and a neurodegenerative or neurological disease. In some embodiments, the compound of formula (I), or the pharmaceutical composition of any thereof is used to treat a disease or condition selected from the group consisting of multiple sclerosis, convulsions, epilepsy, and viral encephalitis. In some embodiments, the compound of formula (I), or the pharmaceutical composition of any thereof is used to treat a disease or condition that involves excess and/or aberrant glutamine activity. In such aspects, the use involves inhibiting the excess and/or aberrant glutamine activity when the compound of formula (I), or the pharmaceutical composition of any thereof, is used to treat the disease or condition.

IV. General Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group on a molecule, provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted at one or more positions).

Where substituent groups or linking groups are specified by their conventional chemical formulae, written from left to right, they equally encompass the chemically identical substituents that would result from writing the structure from right to left, e.g., —CH$_2$O— is equivalent to —OCH$_2$—; —C(=O)O— is equivalent to —OC(=O)—; —OC(=O)NR— is equivalent to —NRC(=O)O—, and the like.

When the term "independently selected" is used, the substituents being referred to (e.g., R groups, such as groups $R_1$, $R_2$, and the like, or variables, such as "m" and "n"), can be identical or different. For example, both $R_1$ and $R_2$ can be substituted alkyls, or $R_1$ can be hydrogen and $R_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless otherwise explicitly defined, a "substituent group," as used herein, includes a functional group selected from one or more of the following moieties, which are defined herein:

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, isopropyl, cyclopropyl, allyl, vinyl, n-butyl, tert-butyl, ethynyl, cyclohexyl, and the like.

Further, more generally, a "carbyl" refers to a carbon atom or a moiety comprising one or more carbon atoms acting as a bivalent radical.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_1$-$C_{10}$ means one to ten carbons, including 1, 2, 3, 4, 5, 6, 7, 8, 9, and 10 carbons). In particular embodiments, the term "alkyl" refers to $C_{1-20}$ inclusive, including 1, 2, 3, 4, 5, 6, 7, 8, 9, 10, 11, 12, 13, 14, 15, 16, 17, 18, 19, and 20 carbons, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_{25}$—S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, —CH=CH—N($CH_3$)—$CH_3$, O—$CH_3$, —O—$CH_2$—$CH_3$, and —CN. Up to two or three heteroatoms may be consecutive, such as, for example, —$CH_2$—NH—O$CH_3$ and —$CH_2$—O—Si($CH_3$)$_3$.

As described above, heteroalkyl groups, as used herein, include those groups that are attached to the remainder of the molecule through a heteroatom, such as —C(O)NR', —NR'R", —OR', —SR, —S(O)R, and/or —S(O$_2$)R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, unsubstituted alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl," by themselves or in combination with other terms, represent, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{1-20}$ inclusive straight or branched hydrocarbon moiety having at least one carbon-carbon double bond by the removal of a single hydrogen molecule. Alkenyl groups include, for example, ethenyl (i.e., vinyl), propenyl, butenyl, 1-methyl-2-buten-1-yl, pentenyl, hexenyl, octenyl, allenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, and heptynyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents."

There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—($CH_2$)$_3$—); cyclohexylene (—$C_6H_{10}$—); —CH═CH—CH═CH—; —CH═CH—$CH_2$—; —$CH_2CH_2CH_2CH_2$—, —$CH_2$CH═CH$CH_2$—, —$CH_2$CsCCH$_2$—, —$CH_2CH_2$CH($CH_2CH_2CH_3$)$CH_2$—, —($CH_2$)$_q$—N(R)—($CH_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—($CH_2$)$_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms also can occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently. Aryls include phenyl ($C_6$), naphthyl ($C_{10}$), and biphenyl ($C_{12}$).

The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

In further embodiments, the term "heteroaryl" refers to a $C_5$-$C_{20}$ aromatic ring wherein at least one carbon atom is replaced by a heteroatom selected from O, S, N, optionally substituted by at least one substituent selected from the group consisting of $C_1$-$C_6$ alkyl, hydroxy, $C_1$-$C_4$ alkoxy, mercapto, $C_1$-$C_4$ alkylthio, amino, —NH($C_1$-$C_6$ alkyl), —N($C_1$-$C_6$ alkyl)$_2$, —O($C_6$-$C_{12}$ aryl), —N($C_6$-$C_{12}$ aryl)$_2$, —NH($C_6$-$C_{12}$ aryl), —S($C_6$-$C_{12}$ aryl), halogen, —$CF_3$, —$SO_3H$, —COOH, —COO($C_1$-$C_8$ alkyl), —$SO_2NH_2$, —$SO_2NH$($C_1$-$C_6$ alkyl or $C_6$-$C_{12}$ aryl), —CN, —$NO_3$, —C(O)($C_1$-$C_5$ alkyl), —C(O)($C_6$-$C_{12}$ aryl), —N($C_1$-$C_6$ alkyl or H)C(O)($C_1$-$C_6$ alkyl or H), —C(O)N($C_1$-$C_6$ alkyl or H)$_2$.

Exemplary heteroaryls include, but are not limited to, pyridyl, pyrimidinyl, pyrazinyl, furanyl, thienyl, pyrazolyl, oxazolyl, thiazolyl, isothiazolyl, isoxazolyl, pyrrolyl, imidazolyl, indolyl, indolinolyl, and imidazopyridazinyl.

In further embodiments, the term "aryl" also can refer to $C_6$-$C_{14}$ aryl, optionally substituted by at least one substituent selected from the group consisting of $C_1$-$C_6$ alkyl, hydroxy, $C_1$-$C_4$ alkoxy, mercapto, $C_1$-$C_4$ alkylthio, amino, —NH($C_1$-$C_6$ alkyl), —N($C_1$-$C_6$ alkyl)$_2$, —O($C_6$-$C_{12}$ aryl), —N($C_6$-$C_{12}$ aryl)$_2$, —NH($C_6$-$C_{12}$ aryl), —S($C_6$-$C_{12}$ aryl), halogen, —$CF_3$, —$SO_3H$, —COOH, —COO($C_1$-$C_8$ alkyl), —$SO_2NH_2$, —$SO_2NH$($C_1$-$C_6$ alkyl or $C_6$-$C_{12}$ aryl), —CN, —$NO_3$, —C(O)($C_1$-$C_8$ alkyl), —C(O)($C_6$-$C_{12}$ aryl), —N($C_1$-$C_6$ alkyl or H)C(O)($C_1$-$C_6$ alkyl or H), —C(O)N ($C_1$-$C_6$ alkyl or H)$_2$.

For brevity, the term "aryl" when used in combination with other terms (e.g., aryloxy, arylthioxy, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(l-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g., "3 to 7 membered"), the term "member" refers to a carbon or heteroatom.

Further, a structure represented generally by the formula:

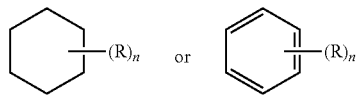

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

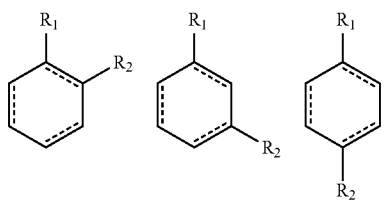

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol ( ⌇⌇⌇⌇ ) denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl," "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R"', —OC(O)R', —C(O)R', —CO$_2$R', —C(O)NR'R", —OC(O)NR'R", —NR"C(O)R', —NR'—C(O)NR"R"', —NR"C(O)OR', —NR—C(NR'R"R"')=NR"", —S(O)R', —S(O)$_2$R', —S(O)$_2$NR'R", —NRSO$_2$R', —CN and —NO$_2$ in a number ranging from zero to (2m'+1), where m' is the total number of carbon atoms in such groups. R', R", R"' and R"" each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R"' and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', —SiR'R"R"', —OC(O)R', —C(O)R', —CO$_2$R', —C(O)NR'R", —OC(O)NR'R", —NR"C(O)R', —NR'—C(O)NR"R"', —NR"C(O)OR', —NR—C(NR'R"R"')=NR"", —NR—C(NR'R")=NR"—S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxo, and fluoro(C$_1$-C$_4$)alkyl, in a number ranging from zero to the total number of open valences on aromatic ring system; and where R', R", R"' and R"" may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R"' and R"" groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R"')$_d$—, where s and d are independently integers of from 0 to 3, and X' is —O—, —NR'—, —S—, —S(O)—, —S(O)$_2$—, or —S(O)$_2$NR'—. The substituents R, R', R" and R"' may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocylic, heterocyclic, or aromatic heterocyclic group as defined herein). As such, the term "acyl" specifically includes arylacyl groups, such as a 2-(furan-2-yl) acetyl)- and a 2-phenylacetyl group. Specific examples of acyl groups include acetyl and benzoyl. Acyl groups also are intended to include amides, —RC(=O)NR', esters, —RC(=O)OR', ketones, —RC(=O)R', and aldehydes, —RC(=O)H.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include C$_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, tert-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl, i.e., $C_6H_5$—$CH_2$—O—. An aralkyloxyl group can optionally be substituted.

"Alkoxycarbonyl" refers to an alkyl-O—C(=O)— group. Exemplary alkoxycarbonyl groups include methoxycarbonyl, ethoxycarbonyl, butyloxycarbonyl, and tert-butyloxycarbonyl.

"Aryloxycarbonyl" refers to an aryl-O—C(=O)— group. Exemplary aryloxycarbonyl groups include phenoxy- and naphthoxy-carbonyl.

"Aralkoxycarbonyl" refers to an aralkyl-O—C(=O)— group. An exemplary aralkoxycarbonyl group is benzyloxycarbonyl.

"Carbamoyl" refers to an amide group of the formula —C(=O)$NH_2$. "Alkylcarbamoyl" refers to a R'RN—C(=O)— group wherein one of R and R' is hydrogen and the other of R and R' is alkyl and/or substituted alkyl as previously described. "Dialkylcarbamoyl" refers to a R'RN—C(=O)— group wherein each of R and R' is independently alkyl and/or substituted alkyl as previously described.

The term carbonyldioxyl, as used herein, refers to a carbonate group of the formula —O—C(=O)—OR.

"Acyloxyl" refers to an acyl-O— group wherein acyl is as previously described.

The term "amino" refers to the —$NH_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R'", wherein R', R", and R'" are each independently selected from the group consisting of alkyl groups. Additionally, R', R", and/or R'" taken together may optionally be —$(CH_2)_k$— where k is an integer from 2 to 6. Examples include, but are not limited to, methylamino, dimethylamino, ethylamino, diethylamino, diethylaminocarbonyl, methylethylamino, isopropylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —C(=O)— group, and can include an aldehyde group represented by the general formula R—C(=O)H.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups. Additionally, terms, such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —$NO_2$ group.

The term "thio" refers to a compound described previously herein wherein a carbon or oxygen atom is replaced by a sulfur atom.

The term "sulfate" refers to the —$SO_4$ group.

The term thiohydroxyl or thiol, as used herein, refers to a group of the formula —SH.

More particularly, the term "sulfide" refers to compound having a group of the formula —SR.

The term "sulfone" refers to compound having a sulfonyl group —$S(O_2)R$.

The term "sulfoxide" refers to a compound having a sulfinyl group —S(O)R.

The term "ureido" refers to a urea group of the formula —NH—CO—$NH_2$.

The term "cyano" refers to the —C≡N group.

The term "triflate" refers to a perfluorosulfonate group having the structure:

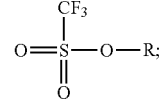

wherein R can be alkyl or aryl. The triflate ion also can be represented as —OTf. Examples of triflate groups include, but are not limited to: methyl triflate (—$CH_2$—OTf), n-butyl triflate (—$CH_2CH_2CH_2CH_2$OTf), and the like.

The term "leaving group" refers to an atom or group of atoms, i.e., a molecular fragment, which is displaced from a molecule through heterolytic bond cleavage, taking with it the electron pair forming the bond between the leaving group and the remainder of the molecule. Examples of leaving groups include, but are not limited to, halogen, cyano, hydroxyl, alkoxyl, acetate, $CF_3$—$S(=O)_2$—O—R—, tosylate

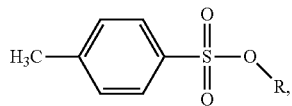

mesylate ($CH_3$—$S(=O)_2$—O—R—), nitrate (—$ONO_2$), phosphate (—$OPO(OH)_2$), carboxylate (—O—CO—R), and phenoxide (—OAr), wherein R is alkylene or arylene and Ar is aryl.

Throughout the specification and claims, a given chemical formula or name shall encompass all tautomers, congeners, and optical- and stereoisomers, as well as racemic mixtures where such isomers and mixtures exist.

Certain compounds of the present disclosure may possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as D- or L- for amino acids, and individual isomers are encompassed within the scope of the present disclosure. The compounds of the present disclosure do not include those which are known in art to be too unstable to synthesize and/or isolate. The present disclosure is meant to include compounds in racemic, scalemic, and optically pure forms. Optically active (R)- and (S)-, or D- and L-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures with the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present disclosure, whether radioactive or not, are encompassed within the scope of the present disclosure.

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (e.g., (+)-tartrates, (−)-tartrates or mixtures thereof including racemic mixtures, succinates, benzoates and salts with amino acids, such as glutamic acid. These salts may be prepared by methods known to those skilled in art. Also included are base addition salts, such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent or by ion exchange. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids, such as arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, +100% in some embodiments+50%, in some embodiments+ 20%, in some embodiments+10%, in some embodiments+ 5%, in some embodiments+1%, in some embodiments+ 0.5%, and in some embodiments+0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Synthesis of Prodrugs of Acivicin

Scheme 1 Synthesis of intermediates 8 and 9

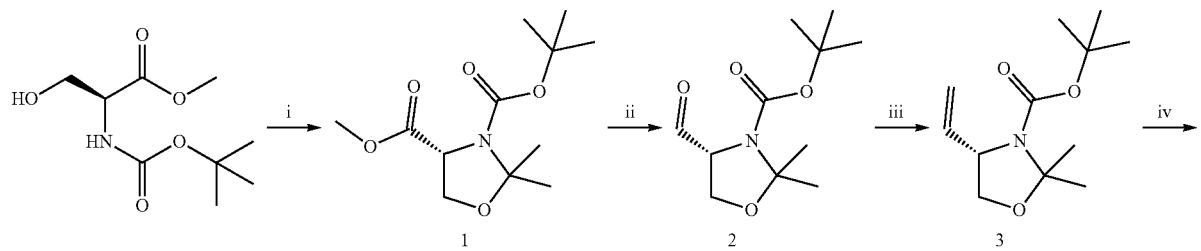

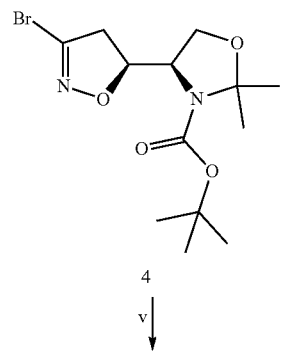

-continued

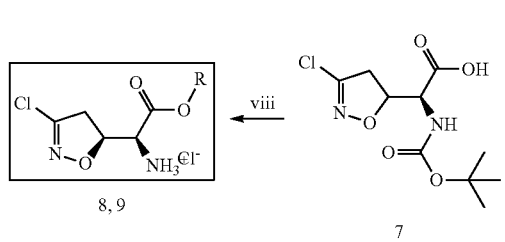 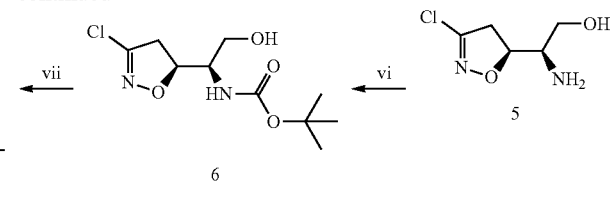

i) 2,2 dimethoxypropane, BF$_3$*Et$_2$O, acetone, rt, 3.5 h, 92% ii) DIBAL-H, DCM, -78° C. to rt, 2 h 80% iii) P$^+$(Ph$_3$)CH$_3$ Br$^-$, BuLi, THF, -78° C. to rt, 21 h, 65% iv) 1,1-dibromoformaldoxime, NaHCO$_3$, EtOAc, rt, 66 h v) 10M HCl (g) in THF, rt, 1 h, 76% vi) Boc$_2$O, Et$_3$N, DCM, 0° C. to rt, 16 h, 67% vii) PDC, DMF, rt, 8 h, 74% viii) SOCl$_2$, iPrOH or EtOH, reflux, 18 h, quant.

Isopropyl 2-amino-2-(3-chloro-4,5-dihydroisoxazol-5-yl)acetate hydrochloride (8)

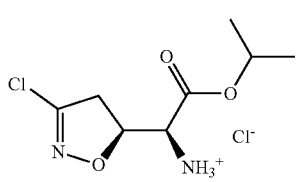

Compound 7 (212 mg, 0.761 mmol) was suspended in dry isopropanol (3 mL). SOCl$_2$ (317 mg, 193 μL, 2.66 mmol, 3.5 equiv.) was added and reaction mixture was refluxed overnight. The organic solvent was evaporated and the residue was co-distilled with PhCH$_3$. The crude product (light brown solid, 196 mg, 100%) was used for further step without any purification.

$^1$H NMR (400 MHz, CD$_3$OD): 1.31 (3H, d, J=6.3), 1.33 (3H, d, J=6.3), 3.51 (1H, dd, J=17.9, 7.5), 3.66 (1H, dd, J=17.9, 11.7), 4.43 (1H, d, J=2.3), 5.14 (1H, sept, J=6.3), 5.23 (1H, ddd, J=11.7, 7.5, 2.3).

$^{13}$C NMR (101 MHz, CD$_3$OD): 21.60, 21.78, 42.49, 56.70, 72.93, 81.16, 151.47, 166.42.

Optical rotation: [α]$^{22}_D$-79.6° (c 0.054, MeOH).

IR (KBr): 3423, 3238, 2982, 2937, 2715, 2591, 1752, 1636, 1489, 1468, 1456, 1415, 1388, 1376, 1339, 1307, 1274, 1238, 1183, 1143, 1104, 1050, 995, 932, 897, 884 cm$^{-1}$.

ESI MS: 243 ([M+Na]$^+$).

HR ESI MS: calcd for C$_8$H$_{13}$O$_3$N$_2$ClNa 243.05069; found 243.05071.

Ethyl 2-amino-2-(3-chloro-4,5-dihydroisoxazol-5-yl)acetate hydrochloride (9)

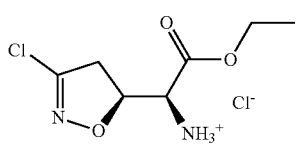

Compound 7 (177 mg, 0.635 mmol) was suspended in dry ethanol (6 mL). SOCl$_2$ (264 mg, 161 μL, 2.22 mmol, 3.5 equiv.) was added and reaction mixture was refluxed overnight. The organic solvent was evaporated and the residue was purified by preparative HPLC (AcN/H$_2$O, TFA) to obtain desired product as colorless solid (45 mg) in 29% yield.

$^1$H NMR (400 MHz, CD$_3$OD): 1.33 (3H, t, J=7.1), 3.50 (1H, dd, J=17.9, 7.2), 3.65 (1H, dd, J=17.9, 11.6), 4.32 (2H, q, J=7.1), 4.44 (1H, d, J=2.5), 5.23 (1H, dddd, J=9.8, 7.2, 2.8, 0.9).

$^{13}$C NMR (101 MHz, CD$_3$OD): 14.20, 42.16, 56.49, 64.35, 81.12, 151.78, 167.02.

Optical rotation: [α]$^{22}_D$-94.0° (c 0.369, CHCl$_3$).

IR (KBr): 3436, 2985, 2947, 2898, 2831, 2631 1744, 1677, 1521, 1469, 1434, 1390, 1371, 1306, 1237, 1207, 1186, 1136, 1042, 1003, 940, 885, 866, 835 cm$^1$.

ESI MS: 207 ([M+H]+).

HR ESI MS: calcd for C$_7$H$_{12}$O$_3$N$_2$Cl 207.05310; found 207.05299.

Scheme 2

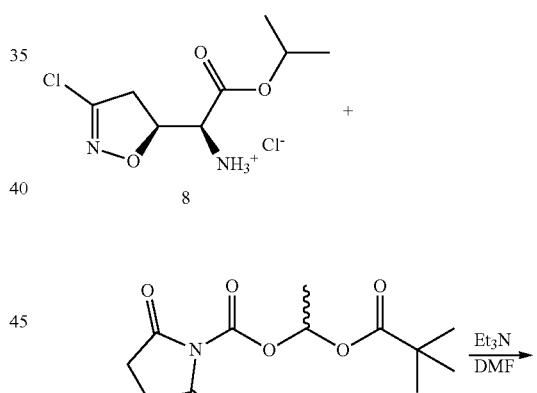

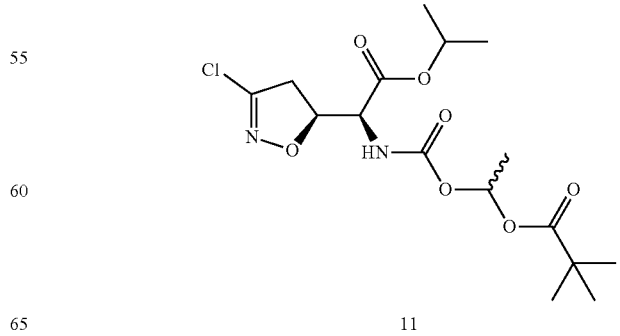

1-(((-1-(3-Chloro-4,5-dihydroisoxazol-5-yl)-2-iso-propoxy-2-oxoethyl)carbamoyl)oxy) ethyl pivalate (11)

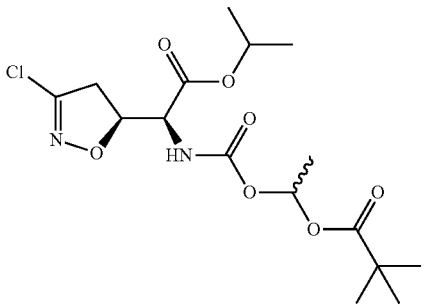 [SMILES: CC(C)OC(=O)[C@@H](NC(=O)OC(C)OC(=O)C(C)(C)C)[C@@H]1CC(Cl)=NO1]

Compound 8 (50 mg, 0.194 mmol) was dissolved in dry DMF (2 mL), NHS ester 10¹ (56 mg, 0.194 mmol) was added and reaction mixture was cooled down to 0° C. Triethylamine (39 mg, 54 µL, 0.389 mmol, 2 equiv.) was added by syringe and the suspension was stirred for 0.5 h at 0° C. and for further 1.5 h at rt. DMF was evaporated and the residue was purified by LC (EtOAc/hexane 1:4). The product 11 was obtained as a light yellow oil (41 mg) in 54% yield.

¹H NMR (400 MHz, CDCl₃): 1.18 (9H, s), 1.25 (9H, s), 1.25-1.28 (6H, m), 1.46 (3H, d, J=5.4), 3.29-3.49 (2H, m), 4.33-4.47 (1H, m), 4.97-5.13 (2H, m), 5.77 (1H, dd, J=12.4, 7.9), 6.77 (1H, q, J=5.4).

¹³C NMR (101 MHz, CDCl₃): 19.72 19.74, 21.57 (2×C), 21.79 (2×C), 26.97 (2×3C), 38.77 38.79, 41.50 41.59, 57.00 57.06, 70.93 70.95, 82.49 82.73, 89.83 89.87, 149.43 (2×C), 153.63 153.71, 167.27 167.43, 176.56 176.59.

Optical rotation: $[\alpha]^{22}_D$-84.3° (c 0.051, CHCl₃).

IR (CHCl3): 3427, 3031, 2983, 2959, 2928, 2872, 2855, 1740, 1639, 1592, 1507, 1480, 1466, 1462, 1433, 1387, 1378, 1365, 1324, 1297, 1285, 1262, 1231, 1203, 1183, 1163, 1146, 1135, 1101, 1080, 1026, 975, 937, 919, 896, 875, 830, 819 cm¹.

ESI MS: 415 ([M+Na]⁺).

HR ESI MS: calcd for $C_{16}H_{25}O_7N_2ClNa$ 415.12425; found 415.12429.

Scheme 3

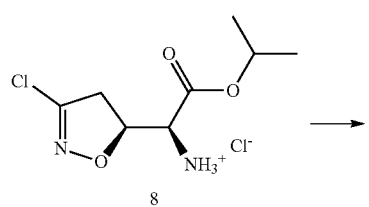

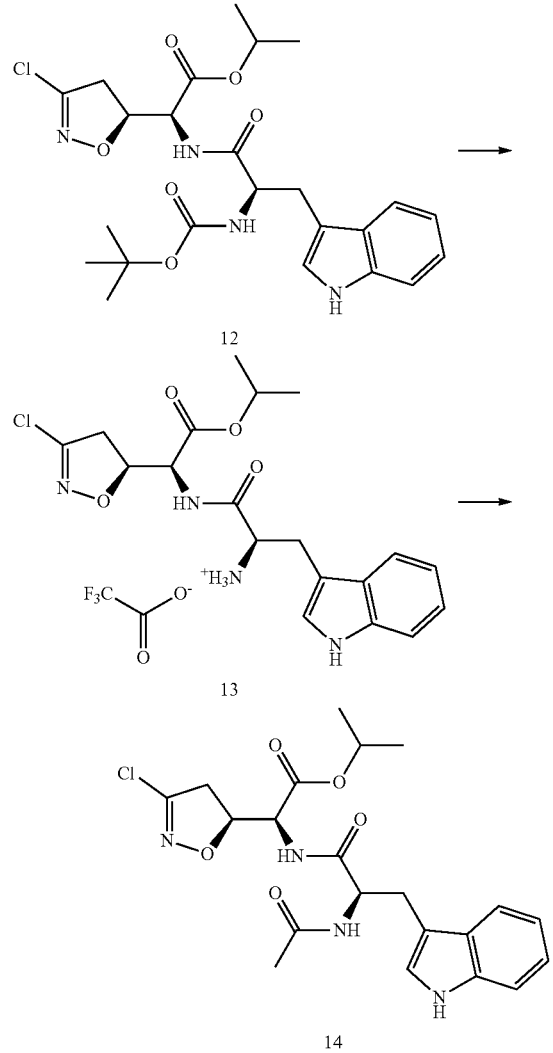

Isopropyl 2-(2-((tert-butoxycarbonyl)amino)-3-(1H-indol-3-yl)propanamido)-2-(3-chloro-4,5-dihydroisoxazol-5-yl)acetate (12)

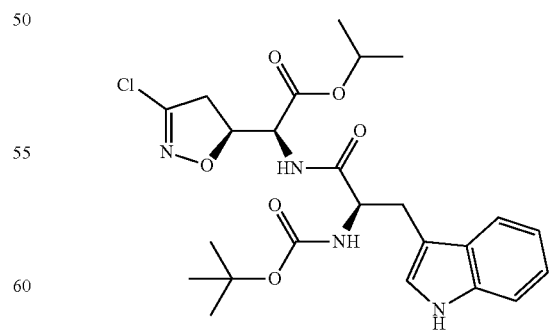

Compound 8 (80 mg, 0.311 mmol) was dissolved in dry DMF (3 mL), triethylamine (47 mg, 65 µL, 0.467 mmol, 1.5 equiv.) followed by Boc-Trp-Osu (137 mg, 0.342 mmol, 1.1 equiv.) were added at 0° C. The suspension was stirred for 0.5 h at 0° C. and for further 16 h at rt. DMF was evaporated and the residue was purified by LC (EtOAc/hexane 1:2). The product 12 was obtained as a colorless solid (71 mg) in 45% yield.

$^1$H NMR (400 MHz, CDCl$_3$): 1.22 (3H, d, J=6.3), 1.24 (3H, d, J=6.3), 1.45 (9H, s), 3.08-3.43 (4H, m), 4.52 (2H, bs), 4.60 (1H, dd, J=7.7, 2.5), 5.00 (1H, sept, J=6.3), 5.20 (1H, bs), 6.78 (1H, d, J=7.8), 7.09 (1H, d, J=2.5), 7.13 (1H, t, J=7.5), 7.21 (1H, t, J=7.5), 7.37 (1H, d, J=8.1), 7.65 (1H, d, J=7.7), 8.36 (1H, bs).

$^{13}$C NMR (101 MHz, CDCl$_3$): 21.50, 21.75, 28.39 (3C), 29.81, 41.53, 55.34, 70.68, 80.42, 82.35 (2C), 110.32, 111.49, 118.89, 119.75, 122.36, 123.36, 127.49, 136.37, 149.42, 155.49, 167.33, 171.86.

Optical rotation: $[\alpha]^{22}_D$-105.8° (c 0.069, CHCl$_3$).

IR (CHCl3): 3478, 3418, 3085, 3061, 3028, 2984, 2931, 2873, 2855, 1736, 1711, 1679, 1621, 1591, 1549, 1490, 1468, 1457, 1434, 1419, 1393, 1387, 1377, 1369, 1340, 1327, 1298, 1286, 1257, 1231, 1200, 1166, 1134, 1103, 1062, 1053, 1027, 1012, 971, 937, 898, 856 cm$^{-1}$.

ESI MS: 529 ([M+Na]$^+$).

HR ESI MS: calcd for C$_{24}$H$_{31}$O$_6$N$_4$ClNa 529.18243; found 529.18260.

1-((1-(3-Chloro-4,5-dihydroisoxazol-5-yl)-2-isopropoxy-2-oxoethyl)amino-3-(1H-indol-3-yl)-1-oxopropan-2-aminium trifluoroacetate (13)

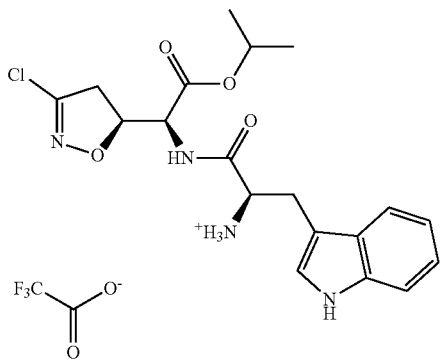 [SMILES: CC(C)OC(=O)[C@@H](NC(=O)[C@H]([NH3+])Cc1c[nH]c2ccccc12)[C@@H]1CC(Cl)=NO1 ; O=C([O-])C(F)(F)F]

Compound 12 (32 mg, 0.063 mmol) was dissolved in dry DCM (1 mL) and reaction mixture was cooled down to 0° C. Trifuoracetic acid (1 mL) was added in 5 minutes and the mixture was stirred for 1 h at 0° C. and for further 1 h at rt. Solvents were evaporated. The product 13 was obtained as a light yellow solid (33 mg) in quantitative yield as a salt of trifluoroacetic acid.

$^1$H NMR (400 MHz, CDCl$_3$): 1.13 (3H, d, J=6.3), 1.15 (3H, d, J=6.3) 3.04 (2H, dq, J=17.8, 9.2), 3.16-3.40 (2H, m), 4.41-4.68 (3H, m), 4.88 (1H, sept, J=6.3), 7.05 (1H, t, J=7.4), 7.06-7.16 (2H, m), 7.32 (1H, d, J=8.1), 7.50 (1H, d, J=7.7), 7.79 (3H, bs), 8.02 (1H, bs), 8.59 (1H, bs).

$^{13}$C NMR (101 MHz, CDCl$_3$): 21.35 (2C), 27.48, 40.60, 54.22, 55.44, 71.63, 81.62, 106.83, 111.87, 115.77 (q, J=287.7), 118.30, 119.98, 122.65, 125.02, 126.89, 136.39, 150.00, 161.52 (q, J=34.8), 167.53, 169.57.

Optical rotation: $[\alpha]^{22}_D$-67.6° (c 0.105, CHCl$_3$).

IR (CHCl3): 3400, 3317, 3224, 3061, 2985, 2938, 2880, 1777, 1736, 1672, 1621, 1593, 1546, 1528, 1459, 1432, 1378, 1361, 1340, 1318, 1297, 1261, 1203, 1183, 1138, 1103, 1011, 966, 931, 896, 837, 818, 799, 747 cm$^{-1}$.

ESI MS: 429 ([M+Na]+).

HR ESI MS: calcd for C$_{19}$H$_{23}$O$_4$N$_4$ClNa 429.13000; found 429.13011.

Isopropyl 2-(2-(acetamido)-3-(1H-indol-3-yl)propanamido)-2-(3-chloro-4,5-dihydroisoxazol-5-yl) acetate (14)

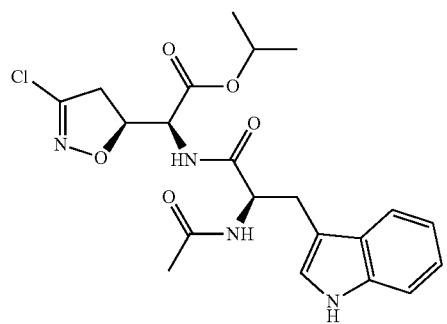 [SMILES: CC(=O)N[C@H](Cc1c[nH]c2ccccc12)C(=O)N[C@H](C(=O)OC(C)C)[C@@H]1CC(Cl)=NO1]

Compound 13 (31 mg, 0.060 mmol) was dissolved in dry DMF (1 mL) and acetanhydride (8 mg, 7.3 μL 1.3 equiv.) followed by triethylamine (18 mg, 25 μL, 0.179 mmol, 3 equiv.) were added at 0° C. The mixture was stirred for 0.5 h at 0° C. and for further 0.5 h at rt. DMF was evaporated and the residue was purified by preparative HPLC (AcN/H$_2$O, TFA). The product 14 was obtained as a colorless solid (19 mg) in 70% yield.

$^1$H NMR (400 MHz, CDCl$_3$): 1.19 (3H, d, J=6.3), 1.21 (3H, d, J=6.3), 2.00 (3H, s), 3.02-3.34 (4H, m), 4.42 (1H, ddd, J=10.9, 7.5, 3.0), 4.57 (1H, dd, J=7.9, 3.0), 4.85 (1H, td, J=7.9, 5.8), 4.99 (1H, sept, J=6.3), 6.64 (1H, d, J=7.5), 6.96 (1H, d, J=7.8), 7.08 (1H, d, J=1.9), 7.11 (1H, t, J=7.4), 7.18 (1H, t, J=7.2), 7.35 (1H, d, J=8.0), 7.62 (1H, d, J=7.8), 8.32 (1H, bs).

$^{13}$C NMR (101 MHz, CDCl$_3$): 21.52, 21.72, 23.04, 28.57, 41.27, 54.31, 55.32, 70.88, 82.01, 110.07, 111.61, 118.75, 119.85, 122.41, 123.49, 127.52, 136.31, 149.49, 167.24, 171.30, 171.52.

Optical rotation: $[\alpha]^{22}_D$-66.1° (c 0.286, MeOH).

IR (CHCl3): 3477, 3420, 3324, 3061, 3027, 2987, 2937, 2880, 2855, 1739, 1661, 1592, 1504, 1467, 1457, 1433, 1420, 1388, 1377, 1340, 1326, 1297, 1260, 1230, 1202, 1182, 1171, 1147, 1134, 1103, 1069, 1040, 1012, 936, 898, 829, 818 cm$^1$.

ESI MS: 471 ([M+Na]+).

HR ESI MS: calcd for C$_{21}$H$_{25}$O$_5$N$_4$ClNa 471.14057; found 471.14067.

Scheme 4

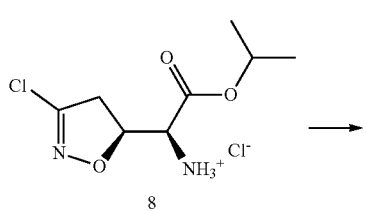

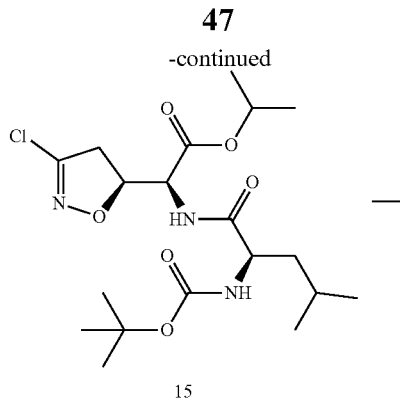

15

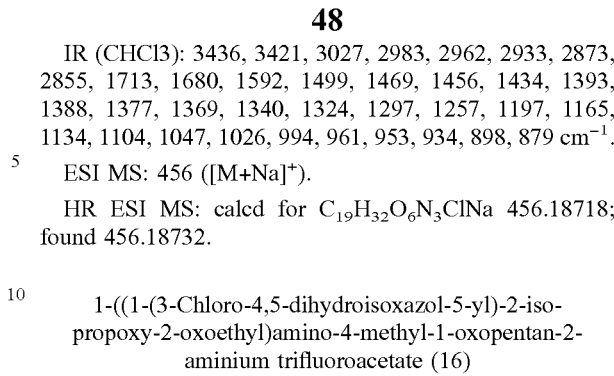

IR (CHCl3): 3436, 3421, 3027, 2983, 2962, 2933, 2873, 2855, 1713, 1680, 1592, 1499, 1469, 1456, 1434, 1393, 1388, 1377, 1369, 1340, 1324, 1297, 1257, 1197, 1165, 1134, 1104, 1047, 1026, 994, 961, 953, 934, 898, 879 cm$^{-1}$.

ESI MS: 456 ([M+Na]$^+$).

HR ESI MS: calcd for $C_{19}H_{32}O_6N_3ClNa$ 456.18718; found 456.18732.

1-((1-(3-Chloro-4,5-dihydroisoxazol-5-yl)-2-isopropoxy-2-oxoethyl)amino-4-methyl-1-oxopentan-2-aminium trifluoroacetate (16)

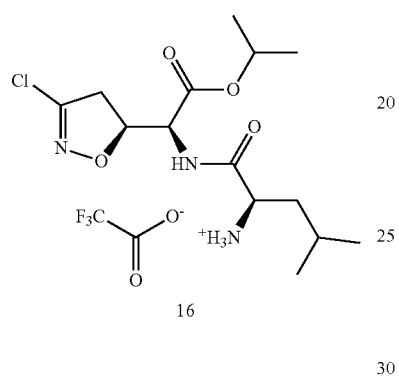

Isopropyl 2-(2-((tert-butoxycarbonyl)amino)-4-methylpentanamido)-2-(3-chloro-4,5-dihydroisoxazol-5-yl)acetate (15)

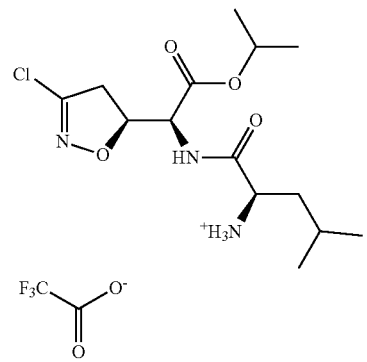

16

Compound 15 (23 mg, 0.053 mmolv) was dissolved in dry DCM (1 mL) and reaction mixture was cooled down to 0° C. Trifuoracetic acid (1 mL) was added in 5 minutes and the mixture was stirred for 1 h at 0° C. Solvents were evaporated. The product 16 was obtained as a colorless solid (24 mg) in quantitative yield as a salt of trifluoroacetic acid.

$^1$H NMR (400 MHz, CDCl$_3$): 0.91 (3H, d, J=6.3), 0.94 (3H, d, J=6.3), 1.24 (3H, d, J=6.8), 1.25 (3H, d, J=6.8), 1.63-1.75 (3H, m), 3.33 (2H, d, J=9.3), 4.29 (1H, bs), 4.90 (1H, d, J=5.6), 5.04 (1H, sept, J=6.3), 5.11 (1H, t, J=9.3), 8.05 (2H, bs), 8.22 (1H, d, J=6.6).

$^{13}$C NMR (101 MHz, CDCl$_3$): 21.46, 21.50, 21.93, 22.26, 24.49, 40.61, 40.63, 52.59, 55.26, 71.49, 81.96, 115.90 (q, J=290.4), 149.78, 161.60 (q, J=35.9), 167.62, 170.35.

Optical rotation: [α]$^{22}_D$-67.8° (c 0.289, MeOH).

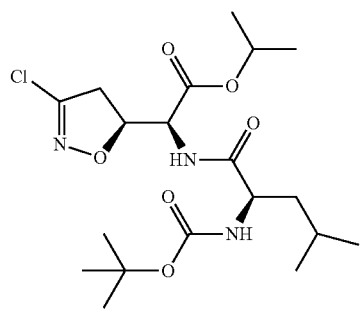 [SMILES: CC(C)C[C@@H](NC(=O)OC(C)(C)C)C(=O)N[C@H](C(=O)OC(C)C)[C@@H]1CC(Cl)=NO1]

Compound 8 (60 mg, 0.233 mmol) was dissolved in dry DMF (2 mL), triethylamine (71 mg, 98 μL, 0.700 mmol, 3 equiv.) followed by Boc-Leu-Osu (115 mg, 0.350 mmol, 1.5 equiv.) were added at rt. The suspension was stirred for 16 h at rt under inert. DMF was evaporated and the residue was purified by LC (EtOAc/hexane 1:4). The product 15 was obtained as a colorless solid (60 mg) in 60% yield.

$^1$H NMR (400 MHz, CDCl$_3$): 0.93 (3H, d, J=6.3), 0.94 (3H, d, J=6.3), 1.26 (6H, dd, J=6.3, 1.3), 1.44 (9H, s), 1.43-1.52 (1H, m), 1.58-1.73 (2H, m), 3.27-3.52 (2H, m), 4.17 (1H, bs), 4.67 (1H, dd, J=7.7, 3.0), 4.89 (1H, d, J=7.6), 4.98 (1H, ddd, J=11.5, 7.4, 3.0), 5.07 (1H, sept, J=6.3), 7.08 (1H, d, J=7.8).

$^{13}$C NMR (101 MHz, CDCl$_3$): 21.58, 21.81, 21.93, 23.10, 24.90, 28.40 (3C), 41.32, 41.63, 53.30, 55.44, 70.76, 80.45, 82.49, 149.41, 155.70, 167.52, 172.83.

Optical rotation: [α]$^{22}_D$-143.1° (c 0.058, CHCl$_3$).

IR (CHCl3): 3322, 3220, 3063, 2982, 2965, 2939, 2876, 2679, 1737, 1673, 1594, 1531, 1469, 1457, 1434, 1389, 1378, 1320, 1296, 1263, 1203, 1183, 1136, 1104, 1071, 974, 942, 929, 896, 837, 799 cm$^1$.

ESI MS: 334 ([M+H]+).

HR ESI MS: calcd for $C_{14}H_{25}O_4N_3Cl$ 334.15281; found 334.15286.

Scheme 5

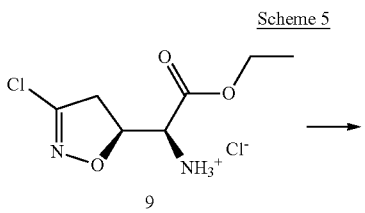

9

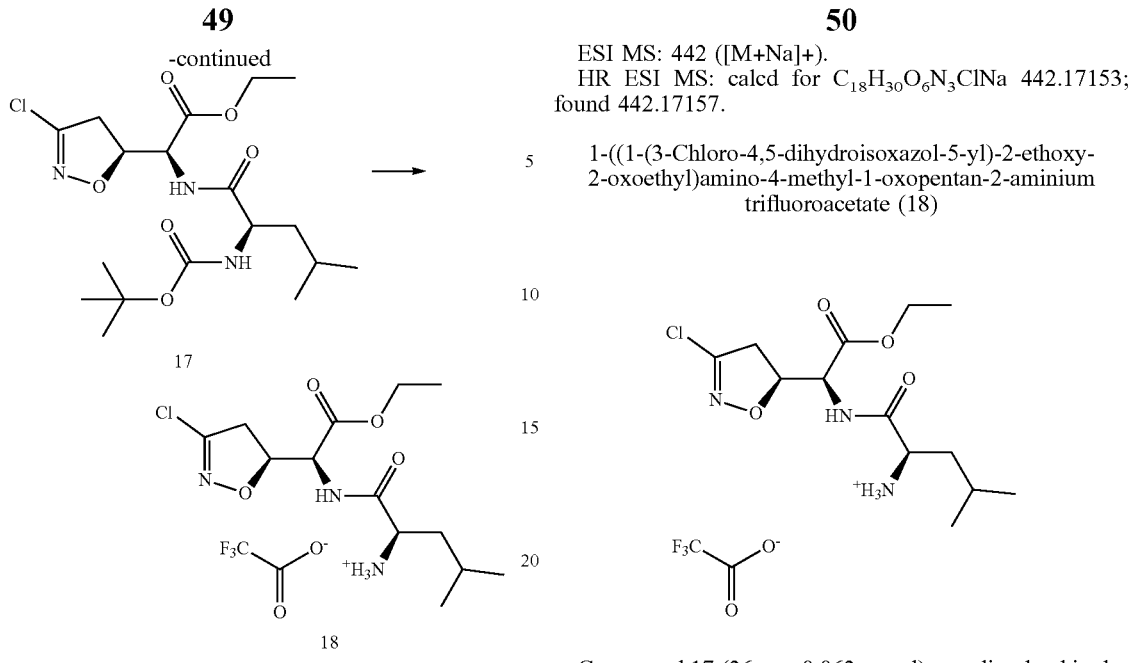

Ethyl 2-(2-((tert-butoxycarbonyl)amino)-4-methyl-pentanamido)-2-(3-chloro-4,5-dihydroisoxazol-5-yl) acetate (17)

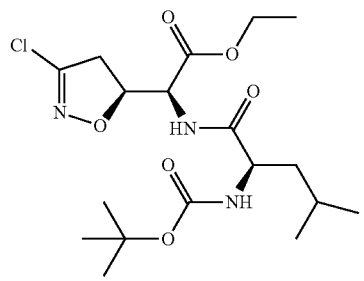 [SMILES: CCOC(=O)[C@@H](NC(=O)[C@@H](CC(C)C)NC(=O)OC(C)(C)C)[C@@H]1CC(Cl)=NO1]

Compound 9 (60 mg, 0.246 mmol) was dissolved in dry DMF (2 mL), triethylamine (124 mg, 172 μL, 1.23 mmol, 5 equiv.) followed by Boc-Leu-Osu (162 mg, 0.494 mmol, 2 equiv.) were added at rt. The suspension was stirred for 16 h at rt under inert. DMF was evaporated and the residue was purified by preparative HPLC (AcN/H$_2$O, TFA). The product 17 was obtained as a colorless solid (52 mg) in 50% yield.

$^1$H NMR (400 MHz, CDCl$_3$): 0.94 (3H, d, J=6.3), 0.95 (3H, d, J=6.3), 1.29 (3H, t, J=7.2), 1.45 (9H, s), 1.47-1.54 (1H, m), 1.58-1.75 (2H, m), 3.40 (2H, dq, J=17.5, 9.1), 4.16 (1H, bs), 4.23 (2H, q, J=7.2), 4.70 (1H, dd, J=7.9, 3.2), 4.84 (1H, d, J=7.5), 4.98 (1H, ddd, J=11.2, 7.0, 3.2), 7.06 (1H, d, J=8.0).

$^{13}$C NMR (101 MHz, CDCl$_3$): 14.12, 21.93, 23.12, 24.92, 28.41 (3C), 41.14, 41.62, 53.31, 55.36, 62.64, 80.56, 82.45, 149.68, 155.69, 168.09, 172.82.

Optical rotation: $[\alpha]^{22}_D$-137.4° (c 0.139, CHCl$_3$).

IR (CHCl3): 3436, 3422, 2982, 2963, 2935, 2873, 2855, 1743, 1708, 1682, 1640, 1591, 1500, 1470, 1456, 1448, 1437, 1394, 1381, 1369, 1325, 1298, 1253, 1195, 1165, 1134, 1047, 1019, 954, 896, 875, 860 cm$^{-1}$.

ESI MS: 442 ([M+Na]+).
HR ESI MS: calcd for C$_{18}$H$_{30}$O$_6$N$_3$ClNa 442.17153; found 442.17157.

1-((1-(3-Chloro-4,5-dihydroisoxazol-5-yl)-2-ethoxy-2-oxoethyl)amino-4-methyl-1-oxopentan-2-aminium trifluoroacetate (18)

Compound 17 (26 mg, 0.062 mmol) was dissolved in dry DCM (1 mL) and reaction mixture was cooled to 0° C. Trifuoracetic acid (1 mL) was added in 5 minutes and the mixture was stirred for 1 h at 0° C. Solvents were evaporated. The product 18 was obtained as a colorless solid (27 mg) in quantitative yield as a salt of trifluoroacetic acid.

$^1$H NMR (400 MHz, CDCl$_3$): 0.91 (3H, d, J=6.0), 0.94 (3H, d, J=6.0), 1.27 (3H, t, J=7.2), 1.61-1.80 (3H, m), 3.34 (2H, d, J=9.1), 4.21 (2H, q, J=7.2), 4.26 (1H, bs), 4.86-4.95 (1H, m), 5.12 (1H, td, J=9.2, 2.9), 5.95 (1H, bs), 8.10 (2H, bs), 8.36 (1H, d, J=7.8).

$^{13}$C NMR (101 MHz, CDCl$_3$): 13.91, 22.02, 22.27, 24.49, 40.63, 40.71, 52.54, 55.20, 63.02, 81.88, 115.78 (q, J=290.0), 149.93, 161.45 (q, J=34.5), 168.28, 170.38.

Optical rotation: $[\alpha]^{22}_D$-73.0° (c 0.185, CHCl$_3$).

IR (CHCl3): 3219, 3064, 2964, 2936, 2876, 2683, 1742, 1673, 1594, 1533, 1470, 1434, 1392, 1373, 1323, 1297, 1261, 1203, 1183, 1137, 1070, 1018, 897, 856, 837, 799 cm$^{-1}$.

ESI MS: 320 ([M+H]$^+$).
HR ESI MS: calcd for C$_{13}$H$_{23}$O$_4$N$_3$Cl 320.13716; found 320.13726.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

Ahluwalia, G. S.; Grem, J. L.; Hao, Z.; Cooney, D. A. Metabolism and action of amino acid analog anti-cancer agents. *Pharmacol Ther* 1990, 46, 243-271.

Alt, J.; Potter, M. C.; Rojas, C.; Slusher, B. S. Bioanalysis of 6-diazo-5-oxo-1-norleucine in plasma and brain by ultra-performance liquid chromatography mass spectrometry. *Anal Biochem* 2015, 474, 28-34.

Barclay, R. K.; Phillipps, M. A. Effects of 6-diazo-5-oxol-norleucine and other tumor inhibitors on the biosynthesis of nicotinamide adenine dinucleotide in mice. *Cancer Res* 1966, 26, 282-286.

Cervantes-Madrid, D.; Romero, Y.; Duenas-Gonzalez, A. Reviving Lonidamine and 6-Diazo-5-oxo-L-norleucine to Be Used in Combination for Metabolic Cancer Therapy. *Biomed Res Int* 2015, 2015, 690492.

Coffey, G. L.; Ehrlich, J.; Fisher, M. W.; Hillegas, A. B.; Kohberger, D. L.; Machamer, H. E.; Rightsel, W. A.; Roegner, F. R. 6-Diazo-5-oxo-L-norleucine, a new tumor-inhibitory substance. I. Biologic studies. *Antibiot Chemother (Northfield)* 1956, 6, 487-497.

D'Andrea, S.; Zheng, Z.; Scola, P. Inhibitors of Hepatitis C Virus. In Google Patents: 2008.

Dion, H. W.; Fusari, S. A.; Jakubowski, Z. L.; Zora, J. G.; Bartz, Q. R. 6-Diazo-5-oxo-L-norleucine, A New Tumor-inhibitory Substance. II. 1 Isolation and Characterization. *J. Am. Chem. Soc.*, 1956, 78, 3075-3077.

Dranoff, G.; Elion, G. B.; Friedman, H. S.; Bigner, D. D. Combination chemotherapy in vitro exploiting glutamine metabolism of human glioma and medulloblastoma. *Cancer Res* 1985, 45, 4082-4086.

Dranoff, G.; Elion, G. B.; Friedman, H. S.; Campbell, G. L.; Bigner, D. D. Influence of glutamine on the growth of human glioma and medulloblastoma in culture. *Cancer Res* 1985, 45, 4077-4081.

Eagan, R. T.; Frytak, S.; Nichols, W. C.; Creagan, E. T.; Ingle, J. N. Phase II study on DON in patients with previously treated advanced lung cancer. *Cancer Treat Rep* 1982, 66, 1665-1666.

Earhart, R. H.; Amato, D. J.; Chang, A. Y.; Borden, E. C.; Shiraki, M.; Dowd, M. E.; Comis, R. L.; Davis, T. E.; Smith, T. J. Phase II trial of 6-diazo-5-oxo-L-norleucine versus aclacinomycin-A in advanced sarcomas and mesotheliomas. *Invest New Drugs* 1990, 8, 113-119.

Earhart, R. H.; Koeller, J. M.; Davis, H. L. Phase I trial of 6-diazo-5-oxo-L-norleucine (DON) administered by 5-day courses. *Cancer Treat Rep* 1982, 66, 1215-1217.

Erickson, J. W.; Cerione, R. A. Glutaminase: a hot spot for regulation of cancer cell metabolism? *Oncotarget* 2010, 1, 734-740.

Eshleman, J. S.; Carlson, B. L.; Mladek, A. C.; Kastner, B. D.; Shide, K. L.; Sarkaria, J. N. Inhibition of the mammalian target of rapamycin sensitizes U87 xenografts to fractionated radiation therapy. *Cancer Res* 2002, 62, 7291-7297.

Fogal, V.; Babic, I.; Chao, Y.; Pastorino, S.; Mukthavaram, R.; Jiang, P.; Cho, Y. J.; Pingle, S. C.; Crawford, J. R.; Piccioni, D. E.; Kesari, S. Mitochondrial p32 is upregulated in Myc expressing brain cancers and mediates glutamine addiction. *Oncotarget* 2015, 6, 1157-1170.

Gallop, M. A.; Xu, F.; Phan, T.; Dilip, U.; Peng, G. Acyloxyalkyl carbamate prodrugs, methods of synthesis and use. In Google Patents: 2008.

Grayzel, A. I.; Seegmiller, J. E.; Love, E. Suppression of uric acid synthesis in the gouty human by the use of 6-diazo-5-oxo-L-norleucine. *J Clin Invest* 1960, 39, 447-454.

Gross, M. I.; Demo, S. D.; Dennison, J. B.; Chen, L.; Chernov-Rogan, T.; Goyal, B.; Janes, J. R.; Laidig, G. J.; Lewis, E. R.; Li, J.; MacKinnon, A. L.; Parlati, F.; Rodriguez, M. L. M.; Shwonek, P. J.; Sjogren, E. B.; Stanton, T. F.; Wang, T.; Yang, J.; Zhao, F. Y.; Bennett, M. K. Antitumor Activity of the Glutaminase Inhibitor CB-839 in Triple-Negative Breast Cancer. *Mol Cancer Ther* 2014.

Harding, J. J. T., M. L.; Munster, P. N.; Le, M. H.; Molineaux, C.; Bennett, M. K.; Mittra, E.; Burris, H. A.; Clark, A. S.; Dunphy, M.; Meric-Bernstam, F.; Patel, M. R.; DeMichele, A.; Infante, J. R. Safety and tolerability of increasing doses of CB-839, a first-in-class, orally administered small molecule inhibitor of glutaminase, in solid tumors. *J Clin Oncol* 2015.

Hensley, C. T.; Wasti, A. T.; DeBerardinis, R. J. Glutamine and cancer: cell biology, physiology, and clinical opportunities. *J Clin Invest* 2013, 123, 3678-3684.

Hofer, A.; Steverding, D.; Chabes, A.; Brun, R.; Thelander, L. *Trypanosoma brucei* CTP synthetase: a target for the treatment of African sleeping sickness. *Proc Natl Acad Sci USA* 2001, 98, 6412-6416.

Hu, X.; Stern, H. M.; Ge, L.; O'Brien, C.; Haydu, L.; Honchell, C. D.; Haverty, P. M.; Peters, B. A.; Wu, T. D.; Amler, L. C.; Chant, J.; Stokoe, D.; Lackner, M. R.; Cavet, G. Genetic alterations and oncogenic pathways associated with breast cancer subtypes. *Mol Cancer Res* 2009, 7, 511-522.

Keicher, J. D.; Roberts, C. D.; Rajwanshi, V. K.; Griffith, R. C.; Zheng, X.; Liehr, S. J. R.; Prhavc, M.; Kim, C. U.; Ray, A. S. Amino tricyclic-nucleoside compounds, compositions, and methods of use. In Google Patents: 2009.

Konopleva, M. Y.; Flinn, I. W.; Wang, E.; DiNardo, C. D.; Bennett, M.; Molineaux, C.; Le, M.; Maris, M.; Frankfurt, O. In *Phase 1 study: Safety and tolerability of increasing doses of cb-839, an orally-administered small molecule inhibitor of glutaminase, in acute leukemia*, Haematologica, 2015; Ferrata Storti Foundation Via Giuseppe Belli 4, 27100 Pavia, Italy: 2015; pp 378-379.

Le, A.; Lane, A. N.; Hamaker, M.; Bose, S.; Gouw, A.; Barbi, J.; Tsukamoto, T.; Rojas, C. J.; Slusher, B. S.; Zhang, H.; Zimmerman, L. J.; Liebler, D. C.; Slebos, R. J.; Lorkiewicz, P. K.; Higashi, R. M.; Fan, T. W.; Dang, C. V. Glucose-independent glutamine metabolism via TCA cycling for proliferation and survival in B cells. *Cell Metab* 2012, 15, 110-121.

Lee, Y. Z.; Yang, C. W.; Chang, H. Y.; Hsu, H. Y.; Chen, I. S.; Chang, H. S.; Lee, C. H.; Lee, J. C.; Kumar, C. R.; Qiu, Y. Q.; Chao, Y. S.; Lee, S. J. Discovery of selective inhibitors of Glutaminase-2, which inhibit mTORC1, activate autophagy and inhibit proliferation in cancer cells. *Oncotarget* 2014, 5, 6087-6101.

Lynch, G.; Kemeny, N.; Casper, E. Phase II evaluation of DON (6-diazo-5-oxo-L-norleucine) in patients with advanced colorectal carcinoma. *Am J Clin Oncol* 1982, 5, 541-543. Magill, G. B.; Myers, W. P. Alterations in calcium metabolism in cancer patients treated with 6-diazo-5-oxo-L-norleucine. *Proc Soc Exp Biol Med* 1956, 93, 314-318.

Magill, G. B.; Myers, W. P.; Reilly, H. C.; Putnam, R. C.; Magill, J. W.; Sykes, M. P.; Escher, G. C.; Karnofsky, D. A.; Burchenal, J. H. Pharmacological and initial therapeutic observations on 6-diazo-5-oxo-1-norleucine (DON) in human neoplastic disease. *Cancer* 1957, 10, 1138-1150.

McDermott, L. A.; Iyer, P.; Vernetti, L.; Rimer, S.; Sun, J.; Boby, M.; Yang, T.; Fioravanti, M.; O'Neill, J.; Wang, L.;

Drakes, D.; Katt, W.; Huang, Q.; Cerione, R. Design and evaluation of novel glutaminase inhibitors. *Bioorg Med Chem* 2016, 24, 1819-1839.

Ostrom, Q. T.; Gittleman, H.; Fulop, J.; Liu, M.; Blanda, R.; Kromer, C.; Wolinsky, Y.; Kruchko, C.; Barnholtz-Sloan, J. S. CBTRUS Statistical Report: Primary Brain and Central Nervous System Tumors Diagnosed in the United States in 2008-2012. *Neuro Oncol* 2015, 17 Suppl 4, iv1-iv62.

Potter, M. C.; Baxter, V. K.; Mathey, R. W.; Alt, J.; Rojas, C.; Griffin, D. E.; Slusher, B. S. Neurological sequelae induced by alphavirus infection of the CNS are attenuated by treatment with the glutamine antagonist 6-diazo-5-oxo-1-norleucine. *J Neurovirol* 2015, 21, 159-173.

Rahman, A.; Smith, F. P.; Luc, P. T.; Woolley, P. V. Phase I study and clinical pharmacology of 6-diazo-5-oxo-L-norleucine (DON). *Invest New Drugs* 1985, 3, 369-374.

Rautio, J.; Kumpulainen, H.; Heimbach, T.; Oliyai, R.; Oh, D.; Jarvinen, T.; Savolainen, J. Prodrugs: design and clinical applications. *Nat Rev Drug Discov* 2008, 7, 255-270.

Ru, P.; Williams, T. M.; Chakravarti, A.; Guo, D. Tumor metabolism of malignant gliomas. *Cancers (Basel)* 2013, 5, 1469-1484.

Schulze, A.; Harris, A. L. How cancer metabolism is tuned for proliferation and vulnerable to disruption. *Nature* 2012, 491, 364-373.

Shukla, K.; Ferraris, D. V.; Thomas, A. G.; Stathis, M.; Duvall, B.; Delahanty, G.; Alt, J.; Rais, R.; Rojas, C.; Gao, P.; Xiang, Y.; Dang, C. V.; Slusher, B. S.; Tsukamoto, T. Design, synthesis, and pharmacological evaluation of bis-2-(5-phenylacetamido-1,2,4-thiadiazol-2-yl)ethyl sulfide 3 (BPTES) analogs as glutaminase inhibitors. *J Med Chem* 2012, 55, 10551-10563.

Sklaroff, R. B.; Casper, E. S.; Magill, G. B.; Young, C. W. Phase I study of 6-diazo-5-oxo-L-norleucine (DON). Cancer Treat Rep 1980, 64, 1247-1251.

Stupp, R.; Hegi, M. E.; Mason, W. P.; van den Bent, M. J.; Taphoorn, M. J.; Janzer, R. C.; Ludwin, S. K.; Allgeier, A.; Fisher, B.; Belanger, K.; Hau, P.; Brandes, A. A.; Gijtenbeek, J.; Marosi, C.; Vecht, C. J.; Mokhtari, K.; Wesseling, P.; Villa, S.; Eisenhauer, E.; Gorlia, T.; Weller, M.; Lacombe, D.; Caimcross, J. G.; Mirimanoff, R. O. Effects of radiotherapy with concomitant and adjuvant temozolomide versus radiotherapy alone on survival in glioblastoma in a randomised phase III study: 5-year analysis of the EORTC-NCIC trial. *Lancet Oncol* 2009, 10, 459-466.

Stupp, R.; Mason, W. P.; van den Bent, M. J.; Weller, M.; Fisher, B.; Taphoorn, M. J.; Belanger, K.; Brandes, A. A.; Marosi, C.; Bogdahn, U.; Curschmann, J.; Janzer, R. C.; Ludwin, S. K.; Gorlia, T.; Allgeier, A.; Lacombe, D.; Caimcross, J. G.; Eisenhauer, E.; Mirimanoff, R. O. Radiotherapy plus concomitant and adjuvant temozolomide for glioblastoma. *N Engl J Med* 2005, 352, 987-996.

Sullivan, M. P.; Beatty, E. C., Jr.; Hyman, C. B.; Murphy, M. L.; Pierce, M. I.; Severo, N. C. A comparison of the effectiveness of standard dose 6-mercaptopurine, combination 6-mercaptopurine and DON, and high-loading 6-mercaptopurine therapies in treatment of the acute leukemias of childhood: results of a coperative study. Cancer *Chemother Rep* 1962, 18, 83-95.

Sullivan, M. P.; Nelson, J. A.; Feldman, S.; Van Nguyen, B. Pharmacokinetic and phase I study of intravenous DON (6-diazo-5-oxo-L-norleucine) in children. *Cancer Chemother Pharmacol* 1988, 21, 78-84.

Tanaka, K.; Sasayama, T.; Irino, Y.; Takata, K.; Nagashima, H.; Satoh, N.; Kyotani, K.; Mizowaki, T.; Imahori, T.; Ejima, Y.; Masui, K.; Gini, B.; Yang, H.; Hosoda, K.; Sasaki, R.; Mischel, P. S.; Kohmura, E. Compensatory glutamine metabolism promotes glioblastoma resistance to mTOR inhibitor treatment. *J Clin Invest* 2015, 125, 1591-1602.

Thangavelu, K.; Chong, Q. Y.; Low, B. C.; Sivaraman, J. Structural basis for the active site inhibition mechanism of human kidney-type glutaminase (KGA). *Sci Rep* 2014, 4, 3827.

Upadhyay, R. K. Drug delivery systems, CNS protection, and the blood brain barrier. *Biomed Res Int* 2014, 2014, 869269.

Weller, M.; van den Bent, M.; Hopkins, K.; Tonn, J. C.; Stupp, R.; Falini, A.; Cohen-Jonathan-Moyal, E.; Frappaz, D.; Henriksson, R.; Balana, C.; Chinot, O.; Ram, Z.; Reifenberger, G.; Soffietti, R.; Wick, W. EANO guideline for the diagnosis and treatment of anaplastic gliomas and glioblastoma. *Lancet Oncol* 2014, 15, e395-403.

Willis, R. C.; Seegmiller, J. E. The inhibition by 6-diazo-5-oxo-1-norleucine of glutamine catabolism of the cultured human lymphoblast. *J Cell Physiol* 1977, 93, 375-382.

Windmueller, H. G.; Spaeth, A. E. Uptake and metabolism of plasma glutamine by the small intestine. *J Biol Chem* 1974, 249, 5070-5079.

Wise, D. R.; Thompson, C. B. Glutamine addiction: a new therapeutic target in cancer. *Trends Biochem Sci* 2010, 35, 427-433.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A prodrug of acivicin, or a pharmaceutically acceptable salt or ester thereof, the prodrug having a structure of formula (I):

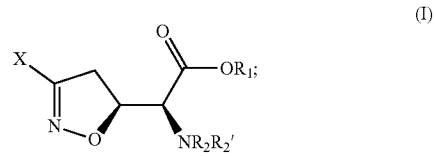

wherein:
  $R_1$ is $C_{3-6}$ branched alkyl; and
  $R_2$ is —C(=O)—Y—$(CR_3R_4)_m$—$NR_5R_6$;
  Y is a bond;
  m=1;
  $R_3$ and $R_4$ are independently H, $C_1$-$C_6$ alkyl or substituted $C_1$-$C_6$ alkyl, aryl or substituted aryl, or

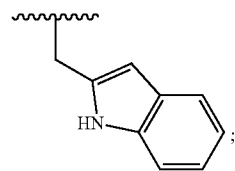 [SMILES: *Cc1cc2ccccc2[nH]1]

$R_5$ and $R_6$ are independently H and alkyl;

$R_2'$ is selected from the group consisting of H, $C_1$-$C_6$ alkyl, substituted $C_1$-$C_6$ alkyl, substituted or unsubstituted succinyl, and substituted or unsubstituted glutamyl, or $R_2$ and $R_2'$ together form a ring structure comprising C(=O)G-C(=O)—, wherein G is selected from the group consisting of $C_1$-$C_8$ alkylene, $C_1$-$C_8$ heteroalkylene, $C_5$-$C_8$ cycloalkylene, $C_5$-$C_{14}$ heteroarylene, and bivalent $C_4$-$C_{10}$ heterocycle, each of which can be optionally substituted; or $R_1$ and $R_2'$ together form a 4-to 6-membered heterocylic ring comprising the oxygen atom adjacent to $R_1$ and the nitrogen atom adjacent to $R_2'$; and X is selected from the group consisting of halogen, cyano, hydroxyl, alkoxyl, and acetate.

2. The prodrug of claim 1, wherein:

$R_3$ is H;

$R_4$ is

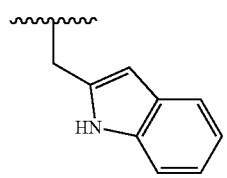 [SMILES: *Cc1cc2ccccc2[nH]1]

or $C_1$-$C_6$ alkyl; and $R_5$ and $R_6$ are each H.

3. A compound, or a pharmaceutically acceptable salt thereof, selected from the group consisting of:

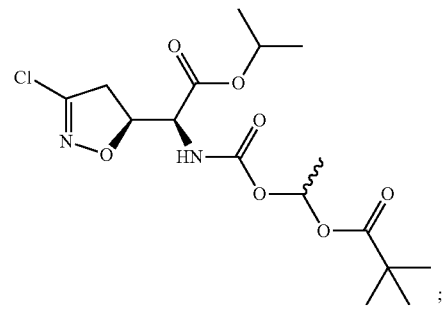

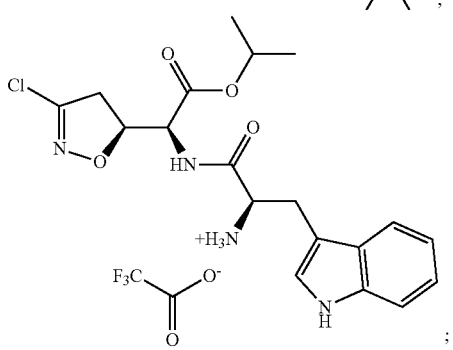

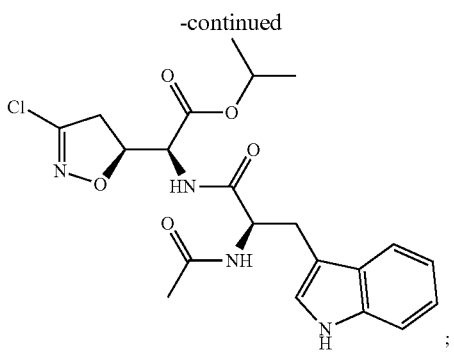

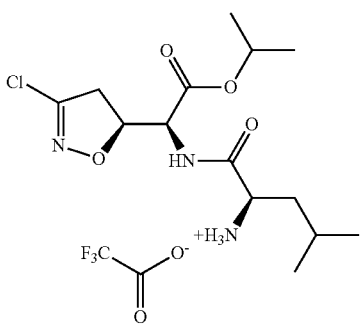

; and

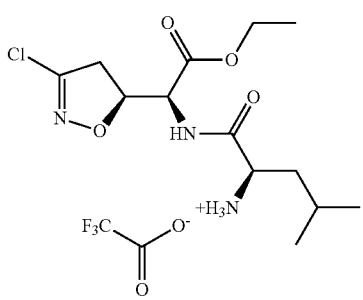

4. A pharmaceutical composition comprising a compound of formula (I) of claim 1, or a pharmaceutically acceptable salt or ester thereof, and a pharmaceutically acceptable carrier, diluent, or excipient.

* * * * *